(12) United States Patent
Stewart et al.

(10) Patent No.: US 6,388,054 B1
(45) Date of Patent: May 14, 2002

(54) ANTI-CANCER COMPOUNDS

(76) Inventors: John M. Stewart, 3690 E. Dartmouth Ave., Denver, CO (US) 80210; Daniel C. F. Chan, 3691 S. Quebec; Lajos Gera, 880 Cherry St., #208, both of Denver, CO (US) 80237; Eunice York, 3102 S. Gaylord St., Englewood, CO (US) 80110; Paul Bunn, 630 Sundown La., Evergreen, CO (US) 80439

( * ) Notice: Subject to any disclaimer, the term of this patent is extended or adjusted under 35 U.S.C. 154(b) by 0 days.

(21) Appl. No.: 09/378,019

(22) Filed: Aug. 19, 1999

Related U.S. Application Data

(60) Provisional application No. 60/097,210, filed on Aug. 20, 1998, and provisional application No. 60/141,169, filed on Jun. 25, 1999.

(51) Int. Cl.[7] .............................. C07K 7/00; C07K 7/02; C07K 7/04
(52) U.S. Cl. ...................... 530/314; 530/328; 530/329; 530/330; 530/332; 530/402; 530/815; 530/816
(58) Field of Search ................................ 530/314, 328, 530/329, 330, 332, 402, 815, 816

(56) References Cited

U.S. PATENT DOCUMENTS

| 5,635,593 A | 6/1997 | Cheronis et al. ............ 530/314 |
| 5,849,863 A | * 12/1998 | Stewart ...................... 530/314 |

FOREIGN PATENT DOCUMENTS

| WO | WO 97/09347 | 3/1997 | ............ C07K/7/18 |

OTHER PUBLICATIONS

Stewart et al., Can. J. Physiol. Pharmacol. 75:719–724, 1997.*

L. Gera, et al., "New Bradykinin Antagonists Having High Potency at Both B1 and B2 Receptors," Peptides: Chemistry, Structure and Biology, Mayflower Scientific Ltd., 1996, pp. 348–349.

D. Chan, et al., "Novel bradykinin antagonist dimers for the treatment of human lung cancers," Immunopharmacology, vol. 33, 1996, pp. 201–204.

* cited by examiner

*Primary Examiner*—F. T. Moezie
(74) *Attorney, Agent, or Firm*—Sheridan Ross P.C.

(57) ABSTRACT

The present invention provides compounds useful to inhibit tumor growth and to induce apoptosis. In general, the anti-cancer agents (ACA) are described by the formula:

$[ACA]_n$-X                                       [Formula I]

wherein X is a linker group having 2–5 functional groups or is absent, n=1, and ACA is selected from the group consisting of Formula II, Formula III, Formula IV, Formula V, and Formula VI, as described herein. Other compounds described herein are defined by the Formula VII, as described herein.

11 Claims, 7 Drawing Sheets

INHIBITION OF GROWTH OF SCLC SHP-77 BY M570/TFA AND M570/HCl IN VIVO
SHP77/NUDE MICE/BKM ANALOGS
5 mg/kg DAILY IP INJECTION

INHIBITION OF GROWTH OF SCLC SHP-77 BY M822 IN VIVO
SHP77/NUDE MICE/BKM ANALOGS
5 mg/kg DAILY IP INJECTION

INHIBITION OF GROWTH OF SCLC SHP-77 BY M638 IN VIVO
SHP77/NUDE MICE/BKM ANALOGS
0.5 mg/kg DAILY IP INJECTION

US 6,388,054 B1

SEQUENCE LISTING

<160> NUMBER OF SEQ ID NOS: 1

<210> SEQ ID NO 1
<211> LENGTH: 9
<212> TYPE: PRT
<213> ORGANISM: Homo sapiens

<400> SEQUENCE: 1

Arg Pro Pro Gly Phe Ser Pro Phe Arg
1               5

ANTI-CANCER COMPOUNDS

The present application claims priority to U.S. Provisional Patent application Ser. No. 60/097,210, filed Aug. 20, 1998 and U.S. Provisional Patent application Ser. No. 60/141,169, filed Jun. 25, 1999. +gi

GOVERNMENT RIGHTS

This invention was made in part with government support under grant numbers NIH HL-26284, awarded by the National Institutes of Health. The government has certain rights to this invention.

FIELD OF THE INVENTION

The present invention relates generally to the field of cancer treatments, as well as to the field of peptide and non-peptide pharmaceutical compounds.

BACKGROUND OF THE INVENTION

Many lung and prostate cancers, of which small cell lung cancer (SCLC) is a prime example, have a neuroendocrine phenotype, and their growth is stimulated by neuropeptides. Antagonists of several peptides (e.g. bradykinin, substance P, bombesin) have been used in experimental treatment of models of SCLC in animals. Among the most potent of the peptides examined thus far, crosslinked dimers of certain bradykinin antagonist peptides have been efficacious both in vitro and in vivo against strains of SCLC and other tumors Chan et al., *Immunopharmacology* 33: 201–204, 1996; Stewart et al., *Can. J Physiol. Pharmacol* 75: 719–724, 1997; Stewart et al., U.S. Pat. No. 5,849,863, issued Dec. 15, 1998). Prostate cancers show a similar neuroendocrine phenotype and are susceptible to neuropeptide antagonists.

SUMMARY OF THE INVENTION

The present invention provides anti-cancer agents (ACA) comprised of a range of novel amino acid derivatives and small peptides having the ability to inhibit growth of SCLC and certain other tumor cell lines (such as non-small cell lung cancer (NSCLC) and prostate cancer) in standard in vitro tests, as well as certain monomeric peptides that show inhibition of tumor growth in vivo. Certain of the peptides have a general structural relationship to carboxy-terminal fragments of bradykinin antagonists, but the non-peptides show no such general relationship. Monomers, dimers, trimers, tetramers, pentamers and cyclized analogs of the novel molecules are described. The new compounds are tested for bradykinin antagonist activity in standard assays, but there is no apparent relationship between bradykinin antagonist activity and cytolytic potency. All of the molecules described possess both hydrophobic (usually aromatic) and basic groups in their structures. Without being held to one particular theory, it appears that the compounds function by stimulation of cell death (apoptosis) in the tumor cells.

The present invention also provides compounds and methods for inhibiting cancer by administering to a subject afflicted with cancer (ie. of the lung or prostate) a therapeutically effective amount of one or more of the compounds herein described.

In general, the anti-cancer compounds are described by the formula:

[ACA]$_n$-X　　　　　　　　　　　　　　　　　[Formula I]

wherein X is a linker having 2–5 functional groups or is absent, n=1–5, and ACA is selected from the group consisting of Formula II, Formula III, Formula IV, Formula V, and Formula VI. Other compounds described herein are defined by the Formula VII. The specifics regarding structure are enumerated in the Detailed Description, Examples and Claims. Certain physical charateristics are enumerated in the Examples as well as the Detailed Description, Examples and Claims.

DETAILED DESCRIPTION OF THE INVENTION

Figure 1:
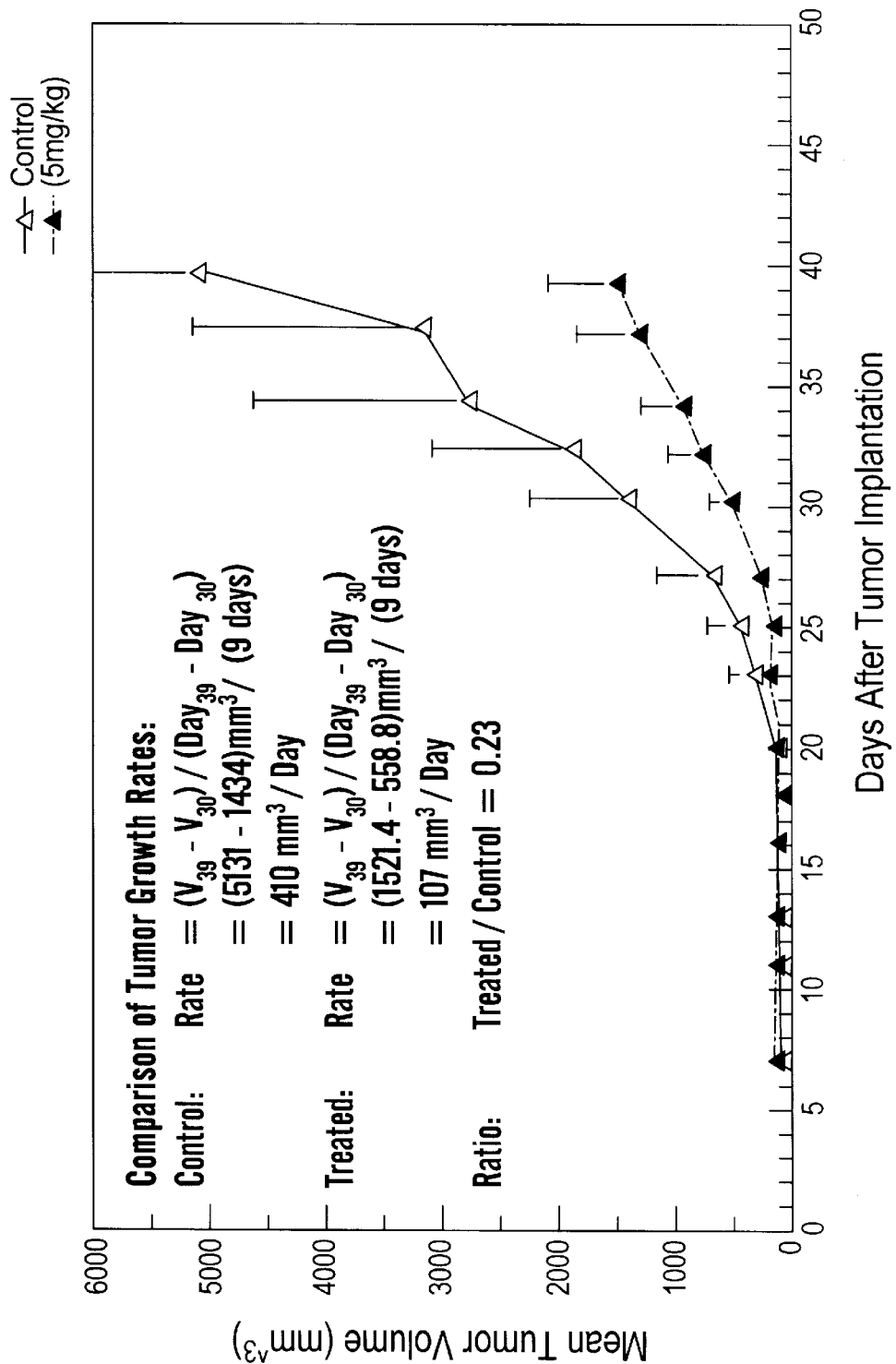
FIG. 1 shows inhibition of growth in vivo of SCLC strain SHP-77 by B10054.

The present invention provides a range of monomeric, dimeric, trimeric, tetrameric, pentameric and cyclic small peptides and peptide mimics that are effective as anti-cancer agents.

In general, the anti-cancer agents (ACA) are described by the formula:

[ACA]$_n$-X　　　　　　　　　　　　　　　　　[Formula I]

wherein X is a linker group having 2–5 functional groups or is absent, n=1, and ACA is selected from the group consisting of Formula II, Formula III, Formula IV, Formula V, and Formula VI, as described herein. Other compounds described herein are defined by the Formula VII, as described herein.

X can be any linking group which does not interfere with the inhibitory activity of the monomer-linker or oligomerized product using bis-imido-esters, bis-maleimidoalkanes such as bis-maleimidohexane, dicarboxylic acids, tricarboxylic acids, tetracarboxylic acids and multi carboxylic acids. Alkane groups may be substituted with alkyl, amino, carboxyl, halogen, hydroxy, mercapto or methoxy groups. Aminoalkyl, aromatic or cycloalkyl polycarboxylic acids, heterocyclic polycarboxylic acids, carboxylic anhydrides and polyoxyethylene linkers may also be used. For C-terminal crosslinking, X may be any diamino or polyamino alkane, cycloalkane, aromatic, heterocyclic diamine, polyamine or other substituted chelating agent (for example: diethylenetriaminepentaacetic dianhydride, ethylenediaminetetraacetic dianhydride, etc.). Polyaminopolycarboxylic acids may also be used to make heteromers (such as ethylenediamine-N,N'-diacetic acid, etc.).

The linkage may be at the N-terminal or the C-terminal or at any position of the ACA sequence through side-chain functional groups. The linker may have any chain length.

For dimers, there is a correspondence between linker length and cytotoxicity. Alkyl chains of 8 carbons or more are preferred, with those of 8 to 18 carbons being most preferred. Examples of preferred dimer linkers for the α-amino at the N-terminal or for a basic side-chain group at any position of ACA include ADA, BTAC, DDD, DDS, DTP, EGS, EOPC, HDD, HFG, PFS, SBEC, SUB, SUIM and TDIM. For dimerization through the C-terminal carboxyl or any side-chain carboxyl in ACA, the preferred linkers include DDA, DEA, EDA, EDP and HAD. Any di-functional molecule can be used.

For trimers, linkers for basic groups include BTAC, BTC, CHTC, CTAC and TREN-(SuC)$_3$; for carboxyl groups, TREN. Any tri-functional molecule can be used.

For tetramers, linkers can be BAPTA, CPTA, EDTA, EGTA, ETTA, or any tetra-functional molecule.

For pentamers, the linker can be DTPA or any pentameric functional molecule. Compounds formed by ACA and a linker X may be homo or hetero multimers.

[Formula II] comprises:

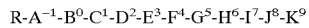

wherein R, A, B, C, D, E, F, G, H, I, J, and K are selected from the following or may be absent, and wherein K is Arg or an Arg derivative:

| R | $A^{-1}$ | $B^0$ | $C^1$ | $D^2$ | $E^3$ | $F^4$ | $G^5$ | $H^6$ | $I^7$ | $J^8$ | $K^9$ |
|---|---|---|---|---|---|---|---|---|---|---|---|
| Absent or | Absent or | Absent or | Absent or | Absent Or | Absent or | Absent or | Absent or | Absent or | Absent or | Absent or | Absent or |
| 3,3DP | DmK | Apc | ApC | MeP | Hyp | Ava | Add | Arg | 2Nal | 2Nal | Arg |
| Aaa | Lys | Arg | Arg | Nig | Pro | BAla | Aud | Gly | DCpG | 2Nal-NH$_2$ | Arg(H) |
| Ac | Lys(εFlu) | DArg | DmK | NMF | | Dpr | CpG | Pac | DF5F | 3,4F2F | Arg-CH$_2$OH |
| Aca | NiK | DLys | NiK | Pro | | Eac | DDMF | Pac | DIgl | 3Pal | Arg-NH$_2$ |
| BApg | PzO | DmK | NiO | | | Gly | DMF | Ser | DPFF | Ac6c | Arg(NO$_2$) |
| Cca | | DniK | PaF | | | | Eac | Thr | DPHe | Aic | Arg-OMe |
| Cin | | DpaF | PzxO | | | | Igl | | DTic | Ana | DArg |
| Dca | | DPzK | | | | | Lys | | Gly | Apb | DArg-NH$_2$ |
| Dcg | | DPzO | | | | | Pac | | mABz | Apb | DArg(NO$_2$) |
| Dhq | | Lys | | | | | Phe | | pABz | Atpc | |
| Dmac | | NiK | | | | | Thi | | Pac | Bip | |
| Dpa | | PaF | | | | | | | PaF(Dcg) | Cmp | |
| F5bz | | PzO | | | | | | | pAmb | CpG | |
| F5c | | DArg-(NO$_2$) | Arg-(NO$_2$) | | | | | | | DhPhe | |
| F5pa | | | | | | | | | | Dpr(Fbz) | |
| Gun | | | | | | | | | | Dpr(Paa) | |
| Hxa | | | | | | | | | | F5F | |
| Mca | | | | | | | | | | F5F-NH$_2$ | |
| Mcg | | | | | | | | | | Hphe | |
| Moti | | | | | | | | | | Ica | |
| Pcc | | | | | | | | | | Igl | |
| Ppa | | | | | | | | | | Igl-NH$_2$ | |
| Pya | | | | | | | | | | Ileu | |
| Saa | | | | | | | | | | Lys(CH$_3$)$_3$ | |
| Ste | | | | | | | | | | Lys(F5bz) | |
| Tfmc | | | | | | | | | | Mapa | |
| | | | | | | | | | | MBC | |
| | | | | | | | | | | MFF | |
| | | | | | | | | | | Nc6G | |
| | | | | | | | | | | Nc7G | |
| | | | | | | | | | | NMF | |
| | | | | | | | | | | OBS | |
| | | | | | | | | | | OBT | |
| | | | | | | | | | | OBY | |
| | | | | | | | | | | OC2Y | |
| | | | | | | | | | | Oic | |
| | | | | | | | | | | Oic-NH$_2$ | |
| | | | | | | | | | | PABz | |
| | | | | | | | | | | Pac | |
| | | | | | | | | | | PaF(F5c) | |
| | | | | | | | | | | PaF(Fbz) | |
| | | | | | | | | | | PaF(Mcg) | |
| | | | | | | | | | | PaF(Ppa) | |
| | | | | | | | | | | PaF(Sin) | |
| | | | | | | | | | | pAmb | |
| | | | | | | | | | | pAPa | |
| | | | | | | | | | | PCF | |
| | | | | | | | | | | PdF | |
| | | | | | | | | | | PFF | |
| | | | | | | | | | | PFF-NH$_2$ | |
| | | | | | | | | | | Phe | |
| | | | | | | | | | | PNF | |
| | | | | | | | | | | Thi | |
| | | | | | | | | | | Tic | |
| | | | | | | | | | | Trp | |
| | | | | | | | | | | Trx | |
| | | | | | | | | | | Tyr | |

[Formula III] comprises:

$$R\text{-}A^1\text{-}B^2\text{-}C^3\text{-}D^4\text{-}E^5\text{-}F^6$$

wherein R, A, B, C, D, E, and F are selected from the following or may be absent, and wherein F is not Arg or an Arg derivative:

| R | $A^1$ | $B^2$ | $C^3$ | $D^4$ | $E^5$ | $F^6$ |
|---|---|---|---|---|---|---|
| Absent or | Absent or | Absent or | Absent or | Absent or | Absent or | Absent or |
| 2,2Dp | DArg | Arg | Add | 2Nal | 1Nal | 2Nal |
| 3,3Dp | DArg(NO$_2$) | | Aud | 3Pal | 2Nal | 3Pal |
| Aaa | | | Ava | Arg | 2Nap | ABza |
| Ac | | | Eac | Arg(Tos) | 3Pal | ABza |
| Aca | | | Lys | Atcp | Apa | Ama |
| Boc | | | Pac | D2Nal | Arg | Ampy |
| Chc | | | | Darg | Arg-NH$_2$ | Ampz |
| Cin | | | | DArg(Tos) | Asp | Apa |
| Ctim | | | | DF5F | Atc | Api |
| Dca | | | | DIgl | Atcp | Aptp |
| Dcg | | | | DPFF | Bip | Aqd |
| Dhq | | | | Eac | BtA | Aqu |
| Dmac | | | | F5F | Cys(Meb) | Arg(H) |
| Dns | | | | Gly | Cys(SO3H) | Arg-CH$_2$OH |
| Dpa | | | | His | D2Nal | Arg-NH$_2$ |
| F5c | | | | Igl | DArg | Arg-OMe |
| F5pa | | | | mABz | DArg-NH$_2$ | Asp |
| F5po | | | | OC2Y | F5F | Asp(Aqu) |
| Gbc | | | | Pac | Glu | Atcp |
| Gun | | | | PFF | Gly | Atmp |
| Hxa | | | | | Igl | AtmpO |
| Mcg | | | | | Inp | Atpm |
| Mse | | | | | Iqa | Cyh |
| Pya | | | | | mABz | Dmab |
| Seb | | | | | MC2Y | Dmm |
| Sin | | | | | N-Dmb-Tyr(Bz)-OMe | Dmp |
| Sul | | | | | OC2Y | Dpea |
| Tfmc | | | | | OCIY | Dpma |
| Tha | | | | | Oic | Dpr(Dcg-2-Nap) |
| | | | | | pABz | Ecap |
| | | | | | PaF(Mes) | F5F-NH$_2$ |
| | | | | | PFF | GaP |
| | | | | | Tic | mA$_2$Bz |
| | | | | | tLeu | mA$_2$Bz(Dcg) |
| | | | | | Trp | mA$_2$Bz(Gun) |
| | | | | | Try | mABz |
| | | | | | Try(Bzl) | Mapp |
| | | | | | Tyr | Matp |
| | | | | | Arg(NO$_2$) | MatpO |
| | | | | | | pABz |
| | | | | | | PaF |
| | | | | | | PaF(Dcg) |
| | | | | | | PaF(Mcg) |
| | | | | | | PaF-NH$_2$ |
| | | | | | | PFF-NH$_2$ |
| | | | | | | PgF |
| | | | | | | PzO |
| | | | | | | Sud |
| | | | | | | Thm |
| | | | | | | Thm |
| | | | | | | Tpac |
| | | | | | | Tpac |
| | | | | | | Tyr(Bz)O |
| | | | | | | Me |

[Formula IV] comprises:

$$A^0\text{-}B^1\text{-}C^2\text{-}D^3\text{-}E^4\text{-}F^5\text{-}G^6\text{-}H^7\text{-}I^8\text{-}J^9\text{-}K^{10}\text{-}L^{11}$$

wherein A, B, C, D, E, F, G, H, I, J, K and L are selected from the following or may be absent:

| $A^0$ | $B^1$ | $C^2$ | $D^3$ | $E^4$ | $F^5$ | $G^6$ | $H^7$ | $I^8$ | $J^9$ | $K^{10}$ | $L^{11}$ |
|---|---|---|---|---|---|---|---|---|---|---|---|
| Absent | Absent | Absent | Absent | Absent | Absent | Absent | Absent | Absent | Absent | Absent | Absent |

-continued

| A⁰ | B¹ | C² | D³ | E⁴ | F⁵ | G⁶ | H⁷ | I⁸ | J⁹ | K¹⁰ | L¹¹ |
|---|---|---|---|---|---|---|---|---|---|---|---|
| or | or | or | or | or | or | or | or | or | or | or | or |
| DArg | Arg<br>DArg | Pro | Lys | Pro | DTrp | Gln<br>DNMF | DTrp | Phe | DTrp | Leu(r) | Leu-NH₂<br>Leu |

[Formula V] comprises:

$$X\text{-}c[A^{-A}\text{-}B^0\text{-}C^1\text{-}D^2\text{-}E^3\text{-}F^4\text{-}G^5\text{-}H^6\text{-}I^7\text{-}J^8\text{-}K^9]$$

wherein X, A, B, C, D, E, F, G, H, I, J, and K are selected from the following or may be absent:

| X | A | B | C | D | E | F | G | H | I | J | K |
|---|---|---|---|---|---|---|---|---|---|---|---|
|  | −1 | 0 | 1 | 2 | 3 | 4 | 5 | 6 | 7 | 8 | 9 |
| Absent | Absent | Absent | Absent | Absent | Absent | Absent | Absent | Absent | Absent | Absent | Absent |
| or | or | or | or | or | or | or | or | or | or | or | or |
| α-Aca | Ava | DArg | Arg | Pro | Hyp | Gly | Add | DArg | DDab | DTrp | Arg |
| 3,3Dp | BAla | DNik | NiK |  |  |  | Aud | Ser | DDpr | F5F | Leu |
|  | DmK | DPaF | PzO |  |  |  | Ava | Thr | DF5F | Lys | NiK |
|  | Glt | DPzK |  |  |  |  | BAla |  | DIgl | Nc7G | PaF |
|  | Lys | DPzO |  |  |  |  | DNMF |  | DLys | Oic | 3Pal |
|  | Suc |  |  |  |  |  | Eac |  | DOm | PaF |  |
|  |  |  |  |  |  |  | Igl |  | DPaF | PFF |  |
|  |  |  |  |  |  |  | Thi |  | Nig | Phe |  |
|  |  |  |  |  |  |  |  |  | Pac |  |  |
|  |  |  |  |  |  |  |  |  | Phe |  |  |

[Formula V] also comprises:

$$X\text{-}c[A^{-1}\text{-}B^0\text{-}C^1\text{-}D^2\text{-}E^3\text{-}F^4\text{-}G^5\text{-}H^6\text{-}I^7\text{-}J^8]\text{-}K^9$$

[Formula V] also comprises:

$$X\text{-}c[A^{-1}\text{-}B^0\text{-}C^1\text{-}D^2\text{-}E^3\text{-}F^4\text{-}G^5\text{-}H^6\text{-}I^7]\text{-}J^8\text{-}K^9$$

wherein the cyclization is via a side chain functional group other than the C-terminal residue and the residues are as described in the immediately preceding table.

[Formula VI] comprises the following cyclic peptides:

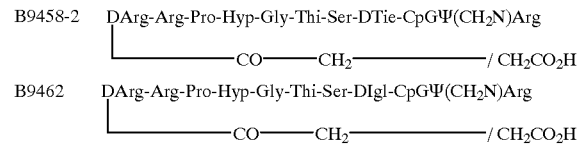

B9458-2  DArg-Arg-Pro-Hyp-Gly-Thi-Ser-DTie-CpGΨ(CH₂N)Arg
         |————————CO————CH₂————————/ CH₂CO₂H

B9462    DArg-Arg-Pro-Hyp-Gly-Thi-Ser-DIgl-CpGΨ(CH₂N)Arg
         |————————CO————CH₂————————/ CH₂CO₂H

ACA can also be those compounds in Table 4.

[Formula VII] comprises:

$$[ACA]_1\text{-}Eac\text{-}Eac\text{-}[ACA]_2$$

wherein [ACA] is defined by Formula I or the compounds in Table 4.

The in vivo inhibitory effects of antagonists may be studied using tumor-bearing nude mice. A tumor model employing nude mice orthotopically implanted with human lung cancer cells wherein the ACA is delivered by intratracheal instillation and aerosol inhalation may be used to evaluate the efficacy and feasibility of these antagonists as a means of treating human lung cancers. Control animals without tumor implantation may also be used to study the general side effects or cytotoxicity of the compounds. It is believed that aerosolized delivery or intratracheal instillation of the agents can produce effective dose accumulation in the area of lesion and reduce the overall systemic toxicity of the compounds in the animals more than when the compound is delivered by systemic administration.

The compounds may be administered topically, or by injection or infusion or as an oral suspension in an appropriate vehicle or as tablets, pills, capsules, caplets or the like, or preferably via intratracheal instillation or aerosol inhalation. The dosage and manner of administration will be defined by the application of the ACA and can be determined by routine methods of clinical testing to find the optimum dose. These doses are expected to be in the range of 0.001 mg/Kg to 100 mg/Kg of active compound.

The compounds are composed of amino acids which may form salts due to their acidic or basic nature, and any pharmacologically acceptable salt derived from the compounds described in this invention such as hydrochlorides, acetates, phosphates, maleates, citrates, benzoates, salicylates, succinates, ascorbates and the like, including HCl, trifluoroacetic acid (TFA), and HOAc, are considered an extension of this invention. A common tactic in medicinal chemistry is to modify known drug substances which are peptide based to form esters or amides which exhibit greater bioavailability. Prodrugs derived from the compounds disclosed here are therefore considered an obvious extension of this invention. Methods for designing and preparing prodrugs are described in detail in the medicinal chemical literature.

Structures and biological activities of peptides and peptide mimics related to bradykinin (BKR) are given in Table 1. Structures and biological activities of compounds not related to bradykinin (BKU) are given in Table 2. Structures and biological activities of cyclic peptides are given in Table 3. Structures of previously described known peptides which we have found to be active against cancers in vivo are included in Table 4. Actions of selected compounds on prostate cancer cell lines are given in Table 5. Abbreviations used are as defined in Table 6.

EXAMPLES

In general, Anti-bradykinin activity was determined by the classical guinea pig ileum assay and on Chinese hamster ovary (CHO) cells expressing cloned human bradykinin B2 receptors. Anti-tumor activity was determined on cultured human cancer cell lines using the standard tetrazolium (MTT) assay. No correlation between anti-bradykinin and cytolytic activity was found among the compounds, indicating that cells are not killed due to inhibition of an essential bradykinin function. Potent compounds were found to stimulate apoptosis in SCLC cells, probably by abnormal activation of the intracellular MEKK pathway.

EXAMPLE I
Synthesis of Peptides

Peptides were synthesized using standard solid phase synthesis methods, well known in the art (Stewart and Young, *Solid Phase Peptide Synthesis*, Pierce Chemical Co., Rockford, Ill., 1984) and were purified by HPLC and were characterized by amino acid analysis (AAA), thin layer chromatography (TLC) and laser desorption mass spectrometry (LDMS). Peptide amides were synthesized on methylbenzhydrylamine (MBHA) resin, which yields amides directly. Peptide methyl esters (OMe) were synthesized by reaction of peptides with 2,2-dimethoxypropane (Rachele, *J. Org. Chem*. 28: 2898, 1963). Cyclic peptides were prepared on resin or in solution with PyAOP and HOAt.

EXAMPLE II
Synthesis of Non-peptides

Non-peptides were synthesized by standard organic chemistry procedures well known in the art. Compounds were purified by HPLC and were characterized by analytical HPLC, TLC, and LDMS.

EXAMPLE III
Synthesis of DDD and SUB Dimers
Synthesis on Resin

Neutralized peptide-resin (0.05 mmole) was treated with 0.15 mmole diisopropylethyl amine (DIEA) and 0.026 mmole dodecanedioyl dichloride or suberoyl dichloride in 2.5 mL dichloromethane (DCM). The suspension was mixed for 5 h, washed with DCM and ethanol and dried. The peptide dimer was cleaved from the resin with HF, and the peptide was extracted and purified Synthesis in Solution Carboxyl-derivatized amino acids or dipeptides were dissolved in dimethyl formamide (DMF) and treated with 10 equivalents of DIEA and 0.55 equivalent of dodecanedioyl dichloride or suberoyl dichloride overnight. The DMF was evaporated in vacuo and the resulting dimer was purified by HPLC.

EXAMPLE IV
Synthesis of EGS, DTP, SBEC and SUB Dimers in Solution

Dimerization in solution proceeded by reacting 1 equivalent of peptide monomer trifluoroacetate, an excess of DIEA and 0.55 equivalent of cross-linking reagent overnight in DMF. The cross-linking agents were purchased from Pierce (EGS dimer, ethylene glycol bis-(succinimidylsuccinate); DTP dimer, dithiobis (succinimidyl propionate); SBEC dimer, bis[(2(succinimidooxycarbonyloxy)ethyl]sulfone; SUB dimer, disuccinimidyl suberate).

EXAMPLE V
Synthesis of Boc-N-cycloheptylglycine (Nc7G)

N-Cycloheptylglycine was synthesized by reductive amination of cycloheptanone with glycine methyl ester following the procedure described in Gera et al., *Immunopharmacology*. 33:174–177 (1996). The crude product was converted to the N-Boc derivative (mp, 89–90° C.).

EXAMPLE VI
Synthesis of TDIM Dimers

Dimethyl tetradecyldiimidate was synthesized from tetradecanedinitrile by the method of De Abreu et al. (*Eur. J Biochem*. 97: 379–387, 1979. One equivalent of peptide TFA salt or other molecule having a free amino group was dissolved in DMF and stirred with 10 equivalents of DIEA and 0.7 equivalent of dimethyl tetradecyldiimidate dihydrochloride overnight at room temperature. DMF was evaporated in vacuo and the dimer was purified. SUIM dimers were prepared similarly, using dimethyl suberimidate.

EXAMPLE VII
Synthesis of B10238: F5C-DArg-Arg-Pro-Hyp-Gly-Igl-Ser-DIgl-Oic-Arg (F5c-B9430)

B10238 was made by standard solid phase synthesis procedures, or by the acylation of B9430 with 2,3,4,5,6-pentafluorocinnamic acid in DMF, using BOP coupling in presence of excess DIEA. The product was purified by HPLC.

EXAMPLE VIII
Synthesis of M822: DDD-(DArg-F5F-Arg)$_2$

Following standard solid phase synthesis procedures, Boc-Arg(Tos) Merrifield synthesis resin was coupled with Boc-F5F, followed by coupling with Boc-DArg(Tos), using HATU as coupling agent. The peptide-resin was deprotected with TFA-DCM and neutralized with TEA. The peptide-resin was then treated with 0.55 equivalent of dodecanedioyl dichloride and 5 equivalents of DIEA in DCM overnight at room temperature. After washing and drying, the resin was cleaved with anhydrous HF, using standard conditions. The peptide was extracted from the resin with 90% acetic acid and purified by preparative HPLC.

EXAMPLE IX
Synthesis of M570 Hydrochloride: F5c-OC2Y-Atmp.HCl

4-Amino-2,2,6,6-tetramethylpiperidine (Aldrich) was coupled with Boc-(O-2,6-dichlorobenzyl)-tyrosine, using BOP in DMF solution. The Boc protecting group was removed by TFA and the product coupled with 2,3,4,5,6-pentafluorocinnamic acid in DMF, using BOP in the presence of excess DIEA at room temperature for 3 h. The DMF was removed in vacuo, the product was extracted into ethyl acetate and the solvent was evaporated. The residue was treated with 0.1–1.0 N HCl or 20% ethanolic HCl. The solvent was removed by evaporation in vacuo at room temperature. The residue was lyophilized from water-dioxane or crystallized from ethanol-ether.

EXAMPLE X
Synthesis of M630: Dmac-OC2Y-Matp.TFA

4-Methylamino-2,2,6,6-tetramethylpiperidine (Matp) was synthesized from 2,2,6,6-tetramethyl-4-piperidone (Aldrich) and methylamine by reductive amination with NaCNBH$_3$. The Matp was coupled with Boc-(O-2,6-dichlorobenzyl)-tyrosine, using BOP in DMF solution. The Boc protecting group was removed by TFA and the product was coupled with 4-(dimethylamino)cinnamic acid in DMF, using BOP in the presence of excess DIEA at room temperature for 3 h. The DMF was removed in vacuo. The product was extracted into ethyl acetate and the solvent was evaporated in vacuo. The crude product was purified by HPLC, giving the TFA salt. The Dmac-OCTY-Matp.TFA salt can be converted to its HCL salt as in Example IX above.

EXAMPLE XI
Synthesis of M638: DDD-(DArg-Igl-Arg-Matp)$_2$

In sequence, Boc-Arg(Tos), Boc-Igl and Boc-DArg(Tos) were coupled to 4-methylamino-2,2,6,6-tetramethylpiperidine (Matp), using BOP as coupling agent in DMF in the presence of excess DIEA at room temperature for 3–5 h. After removal of DMF in vacuo, the product was extracted into ethyl acetate. After evaporation of the solvent, the residue was treated with TFA-DCM to remove the Boc group. TFA was removed in vacuo. The DArg(Tos)-Igl-Arg(Tos)-Matp.TFA was treated with dodecanedioyl dichloride (0.55 equiv) and DIEA (5 equiv) in DCM for 5 h. The protecting groups were cleaved by HF and the lyophilized product was purified by HPLC. The M638.TFA salt was converted to its HCl salt, using 0.1–1.0 N HCl or 20% ethanolic HCl as in Example IX above.

EXAMPLE XII
Synthesis of M590: Atmp-Igl-Pac-α-Sbl-Lys-B9430

In sequence, Boc-Igl, Boc-Pac and mono-methyl sebacate were coupled to 4-amino-2,2,6,6-tetramethylpiperidine (Atmp), using BOP coupling agent in DMF in presence of excess DIEA at room temperature for 3–5 h. DMF was removed in vacuo and the product was extracted into ethyl acetate. After evaporation of the solvent, the methyl ester was hydrolyzed in methanol by 1N NaOH. The crude product (0.025 mmol Atmp-Igl-Pac-Sbl) was coupled to the peptide resin (0.02 mmol Lys(2-CIZ)-DArg(Tos)-Arg(Tos)-Pro-Hyp-Gly-Igl-Ser(Bzl)-DIgl-Oic-Arg(Tos)-Merrifield resin) using BOP/DIEA activation in DMF. The heterodimer peptide was cleaved from the resin with HF, using standard conditions. The peptide was extracted from the resin with acetic acid and purified by preparative HPLC.

EXAMPLE XIII
Synthesis of M872: c[DArg-Arg-Eac-Ser-DF5F-Oic-Arg]

Following standard solid phase synthesis procedures, Boc-DArg(Tos) was coupled to Boc-Arg(Tos) Merrifield synthesis resin, followed in sequence by Boc-Arg(Tos), Boc-Oic, Boc-DF5F, Boc-Ser(Bzl), and Boc-Eac, using HATU as coupling agent. After deprotection with TFA-DCM, the resin was cleaved with anhydrous HF using standard conditions. The peptide was extracted from the resin with 0.1% TFA-H$_2$O/dioxane and lyophilized. The peptide trifluoroacetate was cyclized with three equivalents of PyAOP and HOAt and 20 equivalents of DIEA in DMF at a concentration of $10^{-3}$ M. After removal of the solvent under reduced pressure, the product was lyophilized from dioxane-H$_2$O and purified by HPLC.

EXAMPLE XIV
Synthesis of M678: (Dns-DArg-Igl-Arg)$_2$-DDA

In sequence, Boc-Arg(Tos), Boc-Igl and Boc-DArg(Tos) (2 equivalents) were coupled to 1,10-decanediamine using BOP as a coupling agent in DMF in presence of excess DIEA at room temperature for 3–5 h. DMF was removed in vacuo and the product was extracted into ethyl acetate. The solvent was evaporated in vacuo and the residue was treated with TFA/DCM to remove the Boc group. TFA was removed in vacuo, and the product was treated with dansyl chloride (2 equivalents) and an excess of DIEA in DCM for 5 h. The Tos groups were cleaved by HF and the crude product was purified by HPLC.

EXAMPLE XV
Synthesis of M290: BTAC-(2-Nal-Atmp)$_3$

The benzene-1,3,5-tris-carbamido-ε-caproic acid linker was made from 1,3,5-benzenetricarboxylic acid and N-Boc-ε-caproic acid methyl ester, using the BOP coupling method. The methyl ester was hydrolyzed in methanol by 1N NaOH. The product (1 equivalent BTAC) was coupled to 2-Nal-Atmp (3 equivalents) in DMF, using HATU as coupling agent. The solvent was removed in vacuo, and the residue was purified by HPLC. The BTAC-(2-Nal-Atmp)$_2$-OH was also isolated as a by-product.

EXAMPLE XVI
Synthesis of M1040: EDTA-(OC2Y-ATMP)$_4$

Boc-(O-2,6-dichlorobenzyl)-tyrosine was coupled with 4-amino-2,2,6,6-tetramethylpiperidine overnight in DMF, using BOP as coupling agent in the presence of DIEA. After removal of DMF in vacuo, the residue was extracted into ethyl acetate and treated with TFA/DCM to cleave the Boc group. The TFA/DCM was evaporated in vacuo and the product (OCTY-ATMP) was lyophilized from dioxane/water. Ethylenediaminetetraacetic acid (0.25 equivalent EDTA) was coupled with OC2Y-ATMP trifluoroacetate (1 equivalent) in DMF, using BOP as coupling agent in the presence of DIEA. The solvent was removed in vacuo and the residue was purified by HPLC.

EXAMPLE XVII
Assay of Anti-bradykinin Activity on Guinea Pig Ileum

Male Hartley guinea pigs that had been deprived of food overnight were sacrificed, and sections of terminal ileum, 25 mm in length, were dissected, attached to tissue holders and immersed in 10 ml tissue baths containing Krebs' solution bubbled with 95%O$_2$/5%CO$_2$. Tissues were placed under 1 g tension and incubated for 1 h equilibration. Concentration-effect curves were constructed to bradykinin in the absence and presence of new compounds. Bradykinin showed pD$_2$=7.4, and antagonist B9430 showed pA$_2$=7.9.

EXAMPLE XVIII
Assay of Anti-bradykinin Activity on Cloned Human B2 Receptors

Chinese hamster ovary cells containing cloned and expressed human bradykinin B2 receptors were grown in cell cups of the Cytosensor microphysiometer in Ham's F-12 medium supplemented with sodium pyruvate and 10% FBS (Gibco 11765-054). For assay the cells were transferred to Ham's F-12 without bicarbonate or serum (Gibco 21700-075) and placed in the Cytosensor. Concentration-response curves were constructed to bradykinin in the presence or absence of new compounds. Bradykinin showed pD$_2$=11, and antagonist B9430 showed pA$_2$=10.5

EXAMPLE XIX
Colorimetric Tetrazolium Assay for Cell Survival

Cell growth and survival were measured by a rapid colorimetric assay based on the tetrazolium salt MTT (3-(4, 5-dimethylthiazol-2-yl)-2,5-diphenyl tetrazolium bromide) (Mosmann, *J Immunol. Methods* 65: 55–63, 1983, with minor modifications). Briefly, 1,000 normal lung fibroblasts or normal epithelial BEAS-2B cells, 1,000 or 5,000 viable non-SCLC cells or 10,000 viable SCLC cells were plated in 100 μL of growth medium in 96-well flat-bottomed microtiter plates. Cells were incubated overnight to allow recovery. Compounds to be tested were added to the cells in triplicate in a range of concentrations and the cells were incubated at 37∞C, 5% CO$_2$, with 100% humidity. Control cells were treated in the same way without antagonists. All wells had a final volume of 200 μL. Plates were incubated for 4 days, allowing sufficient time for cell replication and compound-induced cell death to occur. On day 5, 25 μL of a 2 mg/mL solution of MTT (Sigma) dissolved in RMPI- 1640 was added to each well. The plate was incubated for 4 h at 37∞C. The supernate was removed and the blue formazan complex was dissolved by adding 100 μL of 0.02 N HCl in 75% isopropanol to all wells. Absorbance was immediately determined using a scanning multiwell plate reader. B9870 caused 50% cell death at a concentration of 0.15 μM under these conditions.

EXAMPLE XX
Measurement of Apoptosis in Cultured Cells

Apoptosis, also known as programmed cell death, is the phenomenon by which a cell dies following a series of gene-mediated events, in response to a wide range of intracellular and extracellular agents. Apoptosis, a counterpart of mitosis, plays an important role in the development and homeostasis of many organisms and tissues. It serves to regulate cell numbers, to shape developing organisms and as a defense against potentially harmful agents. Apoptosis is not the only mode of cell death. Necrosis is a type of cell death which is nonspecific and frequently occurs when cells are exposed to high doses of toxic agents. Such exposure usually results in the loss of ionic homeostasis. Unlike apoptosis, necrosis does not seem to be genetically influenced.

Apoptotic and necrotic cells have different appearances which allow them to be distinguished microscopically. Necrotic cells and their mitochondria swell, the cell membrane eventually ruptures, and internal organelles become distended. As a result of the membrane rupture, inflammation occurs in the surrounding tissue. In contrast, the nuclei of apoptotic cells become fragmented into several smaller nuclear bodies, which are quickly recognized by phagocytes and engulfed, and no inflammatory response occurs. Therefore, it is useful to develop chemotherapeutics which induce apoptosis, rather than necrosis, in order to avoid inflammation and the toxic agents which are often released from necrotic tumor cells.

We have used differential fluorescent dye uptake and cellular morphology to distinguish viable and dead cells with apoptotic and/or necrotic morphologies. We have used Rhodamine 123 to stain active mitochondria in viable cells, Hoechst 33324 to stain DNA in both viable and dead cells, and Propidium Iodide to stain DNA in dead cells. These cell subpopulations may be distinguished by the different manners in which they take up the fluorescent probes. The dead apoptotic and necrotic subpopulation, which has lost its membrane potential and organelle function, takes up Propidium Iodide and Hoechst 33324. Since the cells in this subpopulation are dead, the mitochondria are not active and thus there is little or no uptake of Rhodamine 123. Under the fluorescence microscope with a DAPI filter, nuclei in these cells appear pinkish in color due to the mixing of both Propidium Iodide and Hoechst 33324 dyes. Necrotic cells have intact nuclei while apoptotic cells have fragmented multi-nucleated bodies. In contrast, the viable apoptotic subpopulation has an intact membrane but inactive mitochondria. As a result, the fragmented multi-nucleated bodies (a hallmark of apoptotic cells) in these cells take up only Hoechst 33324, which gives them a blue appearance under the fluorescence microscope, but are unable to take up Propidium Iodide or Rhodamine 123. The subpopulation of viable cells has both intact cell membranes and active mitochondria. These cells take up both Hoechst 3324 and Rhodamine 123. Microscopically these cells appear to have single normal blue nuclei when examined with a DAPI filter and bright green mitochondria when examined with a FITC filter.

EXAMPLE XXI
Inhibition of Tumor Growth In vivo in Nude Mice

Representative peptide and non-peptide compounds having high in vitro cytotoxic activity were tested against implanted tumors in vivo. Athymic nude mice were implanted subcutaneously with either single cell suspensions (2 million SCLC cells or 1 million NSCLC cells) or with small fragments (3×3 mm) of tumors minced from previously grown nude mouse heterotransplants. On the seventh day after tumor implantation groups of 5 mice bearing implants were injected intraperitoneally daily with the compounds being tested at 1, 5, or 10 mg/kg/day; control animals were injected with an equal volume of isotonic saline. Tumor size was measured with a caliper three times per week. Tumor volume was calculated by the formula:

$$\text{Volume(cc)} = \pi \times (\text{length}) \times (\text{width})^2 / 6$$

Figure 2:
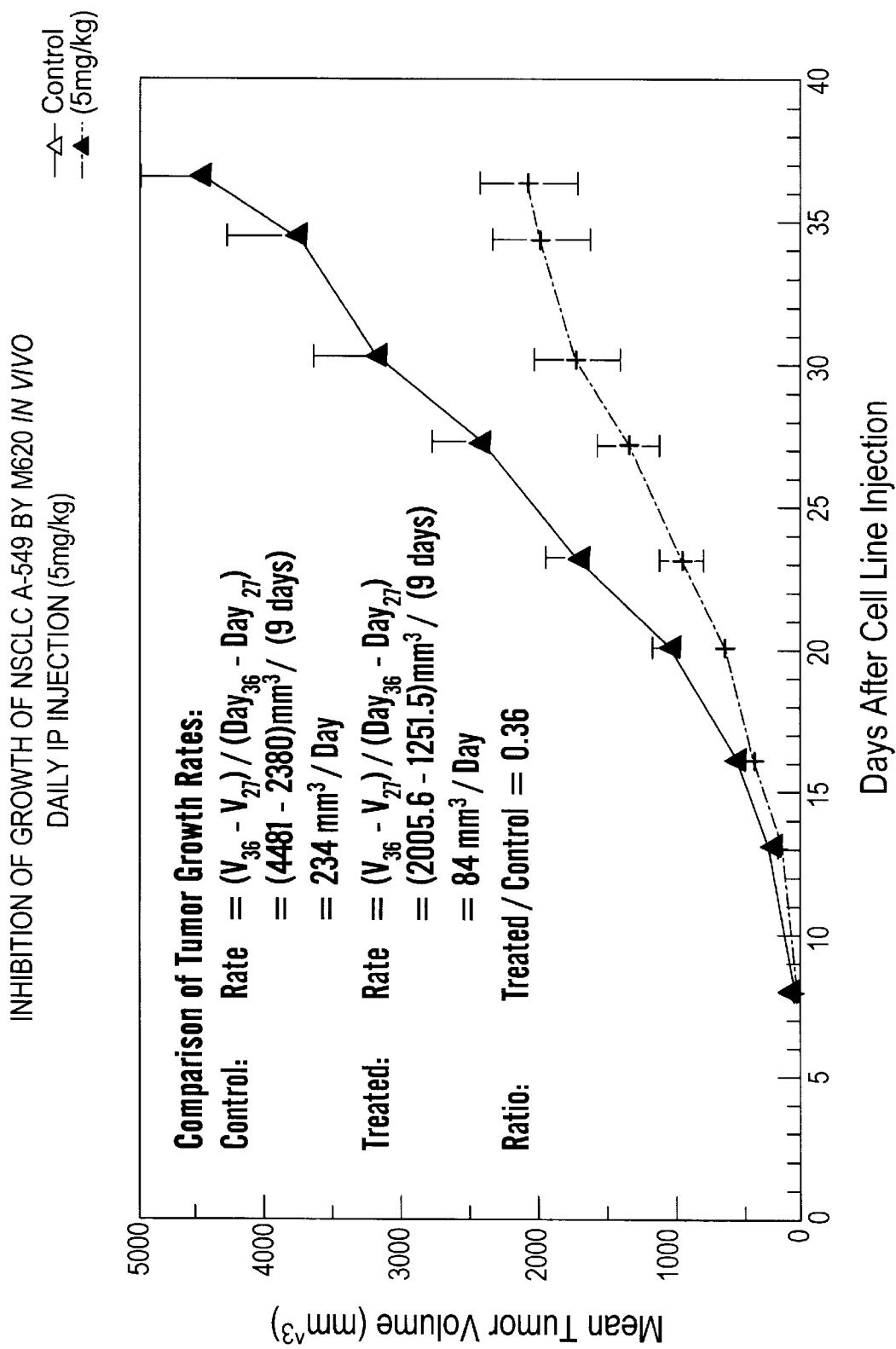
FIG. 2 shows inhibition of growth in vivo of NSCLC strain A-549 by M620.
Figure 3:
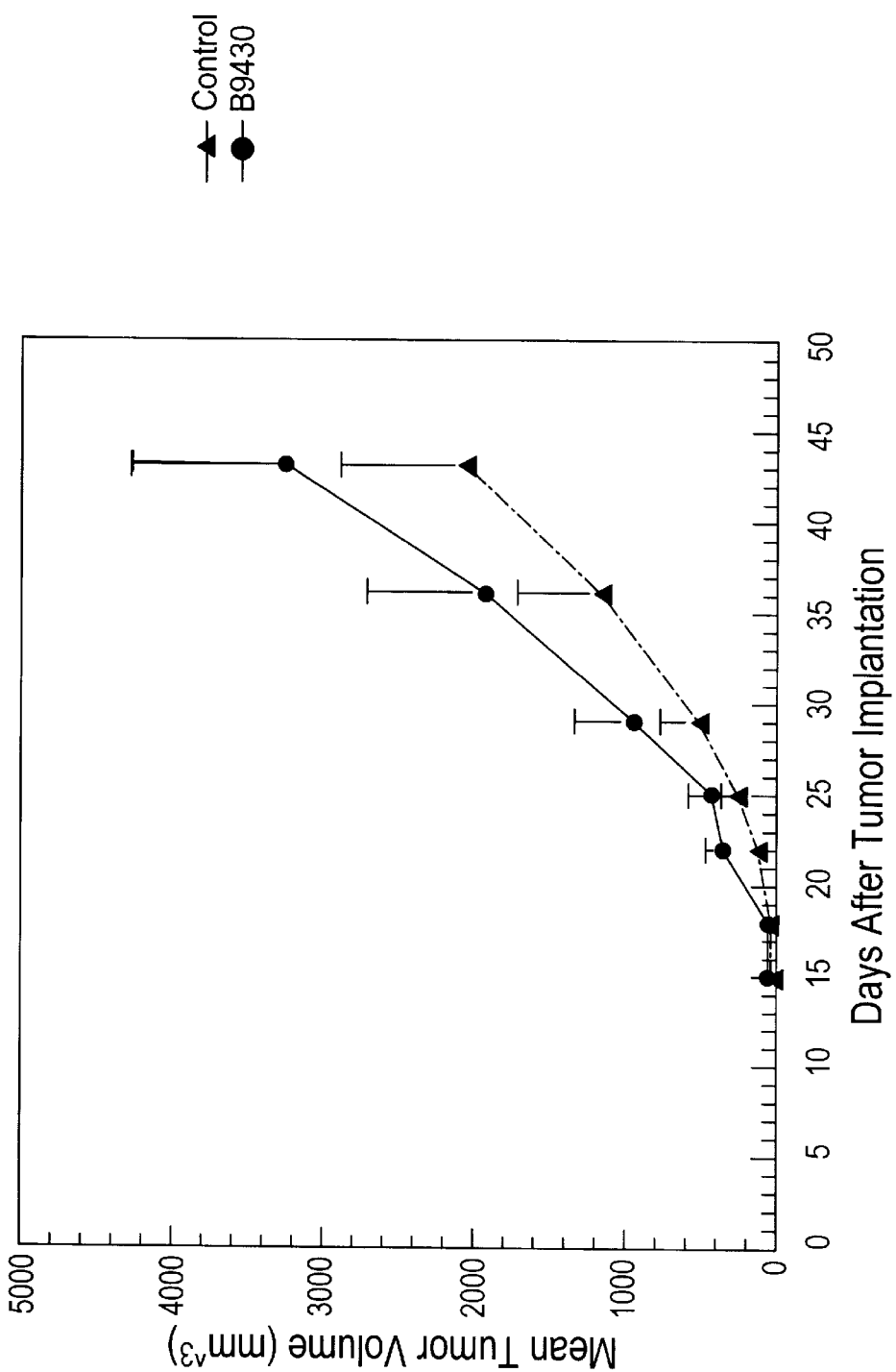
FIG. 3 shows inhibition of growth in vivo of SCLC strain SHP-77 by B9430.
Figure 4:
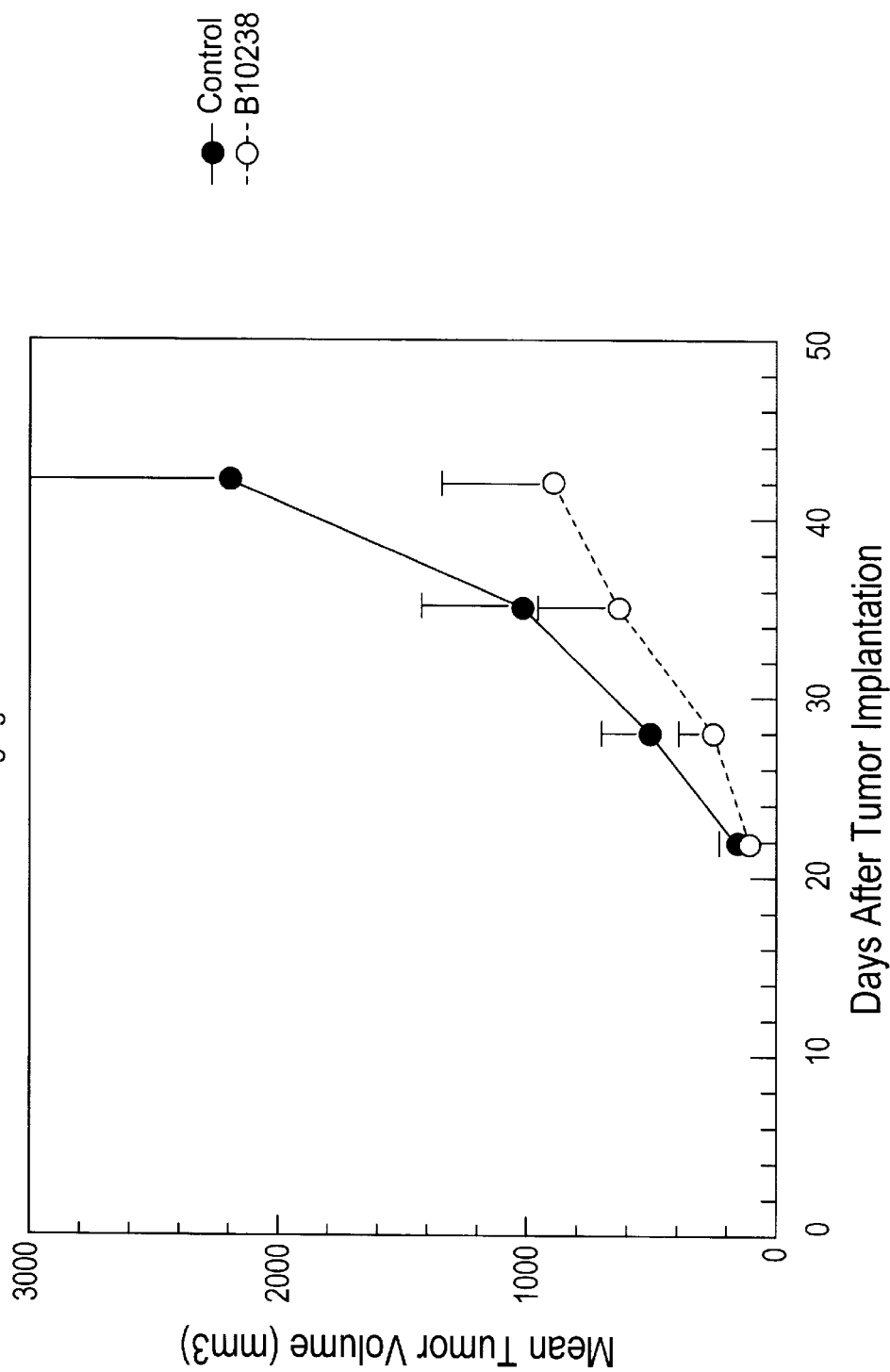
FIG. 4 shows inhibition of growth in vivo of SCLC strain SHP-77 by B10238
Figure 5:
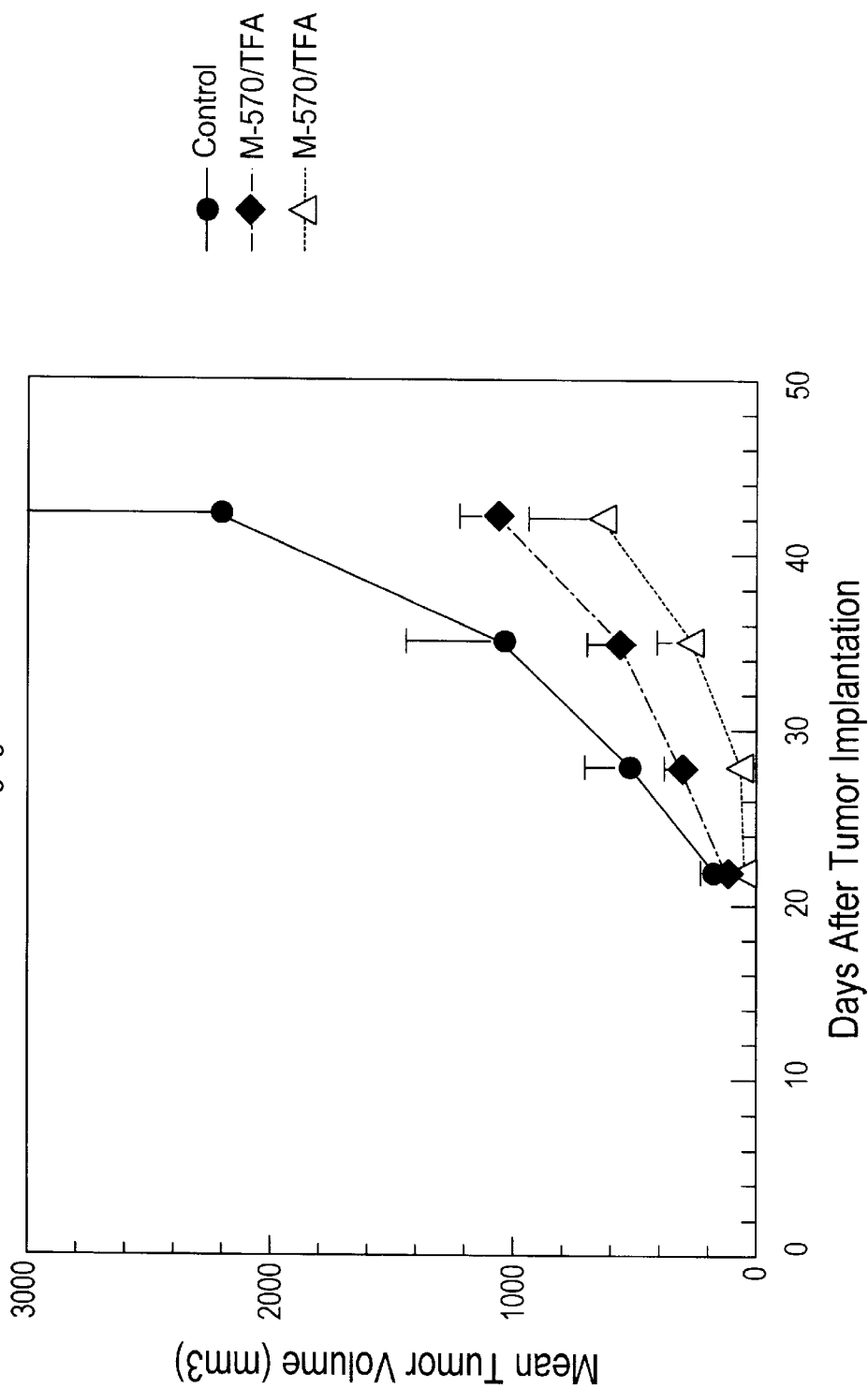
FIG. 5 shows inhibition of growth in vivo of SCLC strain SHP-77 by M570, both as the trifluoroacetate salt and as the hydrochloride salt.
Figure 6:
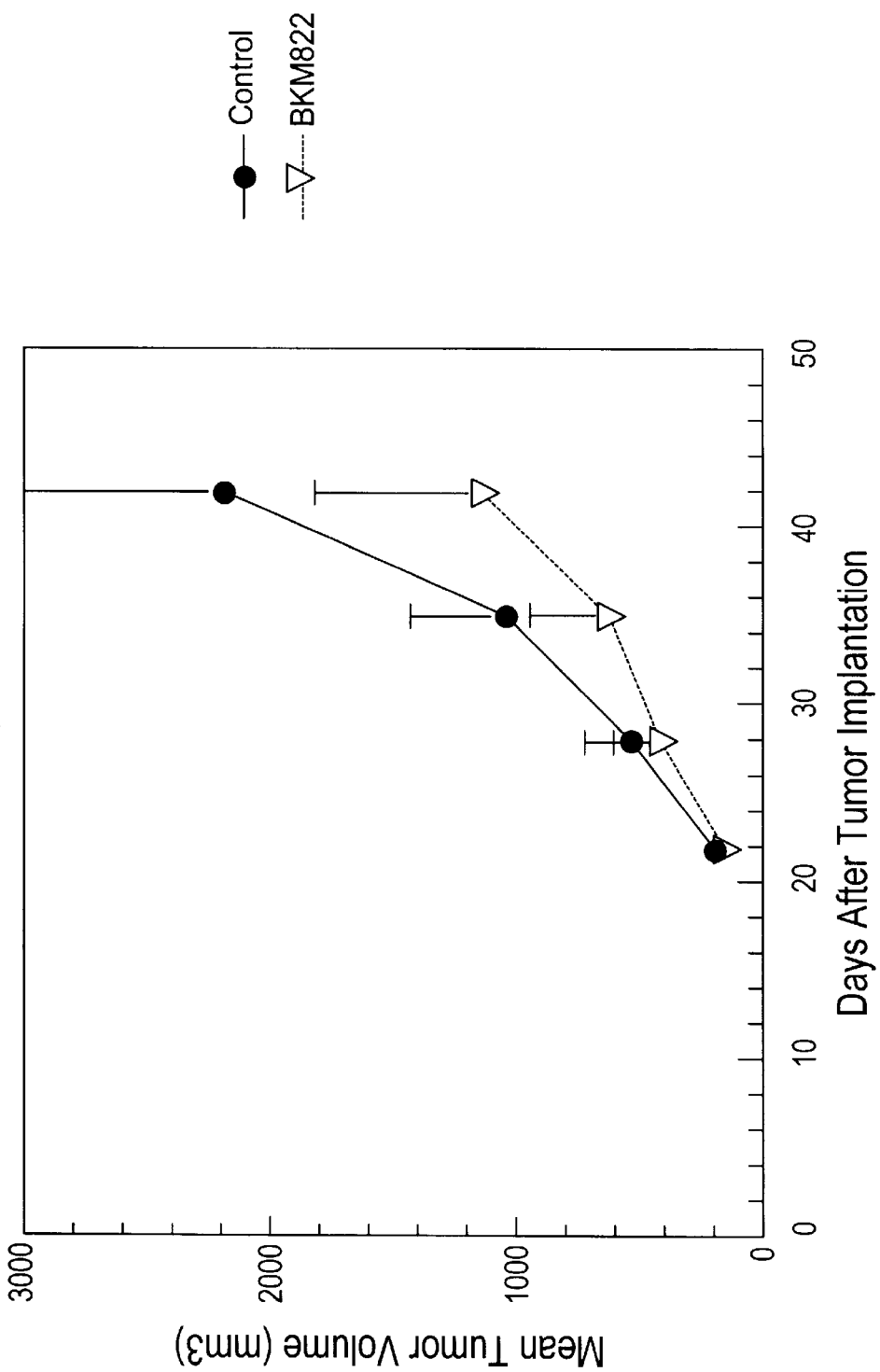
FIG. 6 shows inhibition of growth in vivo of SCLC strain SHP-77 by M822.
Figure 7:
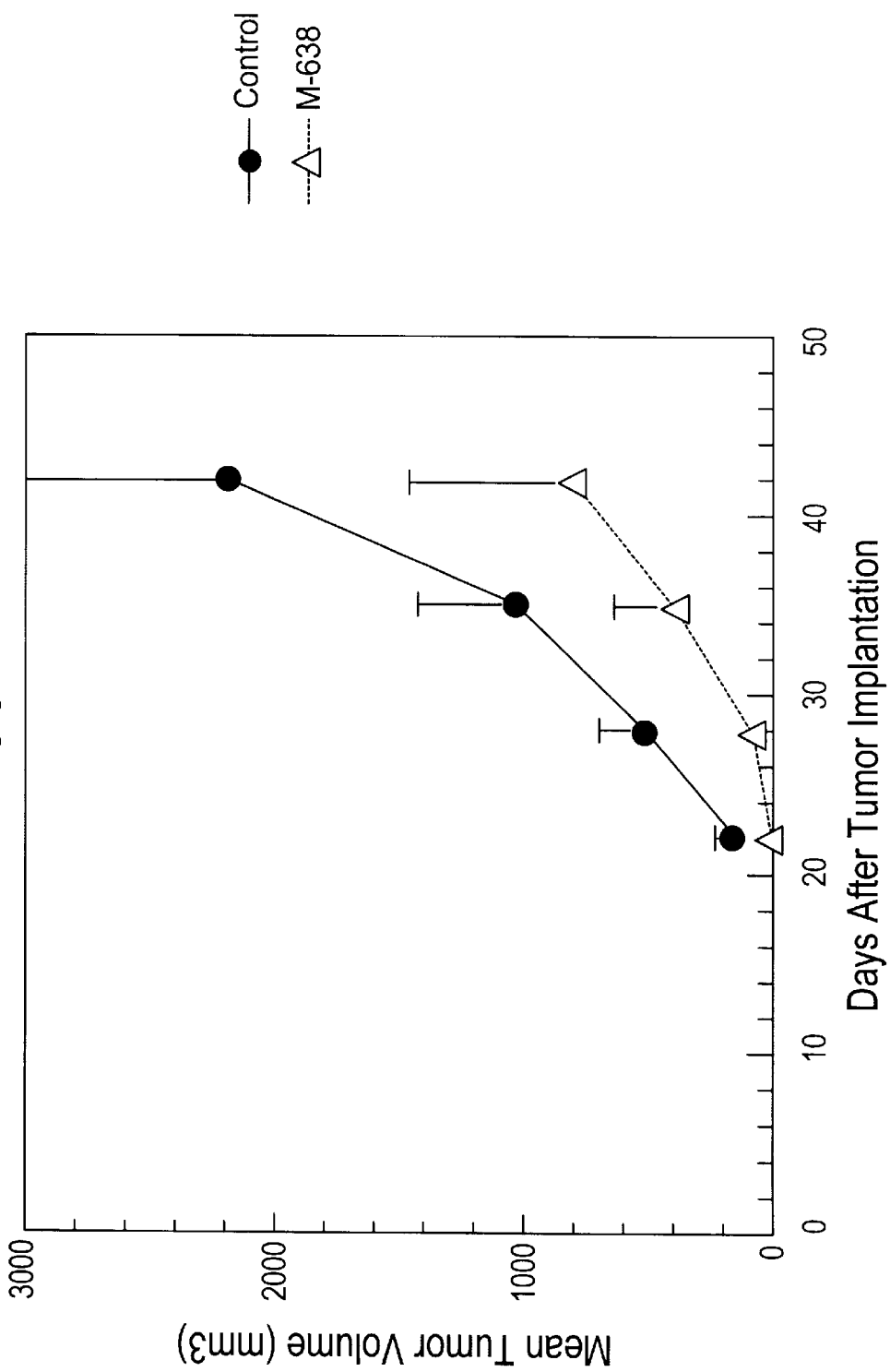
FIG. 7 shows inhibition of growth in vivo of SCLC strain SHP-77 by M638.

Results of representative in vivo tests are given in FIGS. 1–8. For comparison, bradykinin antagonist peptide dimers B9870 and B10054 caused marked inhibition of growth of the SCLC line SHP-77 at a dose of 5 mg/kg/day.

EXAMPLE XXII
Data

Examples of peptides and peptide mimics related to the C-terminal part of bradykinin antagonist peptides and their biological activities on cancer cells and bradykinin responses are given in Table 1.

Many compounds not directly related to the structure of bradykinin were synthesized and tested for anti-tumor and anti-bradykinin activity. These are listed in Table 2.

Cyclic peptides related to bradykinin and bradykinin mimics are reported in Table 3, along with their biological activity on cancer cells and anti-bradykinin activity.

Structures of previously described known peptides which have been found to be active against cancers in vivo are included in Table 4.

Cytotoxic activity in vitro of compounds M570 and M590 against various standard strains of prostate cancer is reported in Table 5.

Standard abbreviations were used for natural amino acids. For non-natural amino acids, derivatizing groups and other chemicals, the abbreviations listed in Table 6 are used.

TABLE 1

ACTIVITIES OF PEPTIDES RELATED TO BRADYKININ STRUCTURE

| NUMBER | STRUCTURE | MTT[a] | GPI[b] | HUMAN[c] |
|---|---|---|---|---|
| BK[d] | Arg-Pro-Pro-Gly-Phe-Ser-Pro-Phe-Arg | | | |
| B9430[d] | DArg-Arg-Pro-Hyp-Gly-Igl-Ser-DIgl-Oic-Arg | 120 | 8.2 | |
| B9870-2[d] | SUIM-(DArg-Arg-Pro-Hyp-Gly-Igl-Ser-DIgl-Oic-Arg) | 0.15 | 8.4 | |

TABLE 1-continued

ACTIVITIES OF PEPTIDES RELATED TO BRADYKININ STRUCTURE

| NUMBER | STRUCTURE | MTT[a] | GPI[b] | HUMAN[c] |
|---|---|---|---|---|
| B8838 | DArg-Arg-Pro-Hyp-Gly-CpG-Ser-DCpG-CpG-Arg | — | 7.0 | |
| B8840 | DArg-Arg-Pro-Hyp-Gly-Phe-Ser-DCpG-CpG-Arg | — | 6.8 | |
| B8858 | DArg-Arg-Pro-Hyp-Gly-Thi-Ser-CpG-DCpG-DArg | — | 5.2 | |
| B8994 | DArg-Arg-Pro-MeP-Gly-CpG-Ser-DCpG-CpG-Arg | — | — | |
| B9074 | Dhq-DArg-Arg-Pro-Hyp-Gly-CpG-Ser-DCpG-CpG-Arg | — | 6.3 | |
| B9126 | Aaa-DArg-Arg-Pro-Hyp-Gly-(D,L)DMF-Ser-DTic-Oic-Arg | — | 6.4 | |
| B9126-2 | Aaa-DArg-Arg-Pro-Hyp-Gly-(D,L)DMF-Ser-DTic-Oic-Arg | — | 7.3 | |
| B9224-2 | Aca-DArg-Arg-Pro-Hyp-Gly-Thi-Ser-(D,L)Igl-Oic-Arg | — | 8.4 | |
| B9882 | α-Sub-Lys(εFlu)-DArg-Arg-Pro-Hyp-Gly-Igl-Ser-DIgl-Oic-Arg<br>    \|<br>    └—DArg-Arg-Pro-Hyp-Gly-Igl-Ser-DIgl-Oic-Arg | — | — | |
| B9914 | Oic-Arg | — | Wk | |
| B9916 | DIgl-Oic-Arg | — | Wk | |
| B9490 | Dcg-DIgl-Oic-Arg | >60 | Wk | |
| B9918 | Ser-DIgl-Oic-Arg | — | — | |
| B9920 | Igl-Ser-DIgl-Oic-Arg | — | — | |
| B9922 | Gly-Igl-Ser-DIgl-Oic-Arg | — | Wk | |
| B9924 | Hyp-Gly-Igl-Ser-DIgl-Oic-Arg | — | — | |
| B9926 | Pro-Hyp-Gly-Igl-Ser-DIgl-Oic-Arg | — | — | |
| B9950 | α-Lys-DArg-Arg-Pro-Hyp-Gly-Igl-Ser-DIgl-Oic-Arg<br>    \|<br>    Sub-Arg-DNMF-DTrp-Phe-DTrp-Leu | 8 | — | |
| B9956 | α-DDD-(Lys-DArg-Arg-Pro-Hyp-Gly-Igl-Ser-DIgl-Oic-Arg)$_2$. | — | — | |
| B9960 | DArg-Arg-Nig-Hyp-Gly-Igl-Ser-DIgl-Oic-Arg | — | 7.7 | |
| B9966 | DArg-Arg-NMF-Hyp-Gly-Thi-Ser-DIgl-Oic-Arg | — | 6.9 | |
| B10010 | DArg-Arg-Pro-Hyp-Gly-Igl-Ser-DIgl-Oic-Nc7G-Arg | — | 7.7 | |
| B10014 | DArg-Arg-Pro-Hyp-Gly-Thi-Ser-DTic-Nc6G-Arg | — | 7.6 | |
| B10054 | DDD-(Lys-DArg-Arg-Pro-Hyp-Gly-Igl-Ser-DIgl-Oic-Arg)$_2$ | 0.3 | 7.1 | |
| B10062 | DArg-Arg-Pro-Hyp-Gly-Igl-Ser-DIgl-Oic-Arg-NH$_2$ | Inact | 7.1 | |
| B10082 | SUIM-(DArg-Arg-Pro-Hyp-Gly-Igl-Ser-DIgl-Oic-Arg-NH$_2$)$_2$ | 0.7 | 7.2 | |
| B10084 | BApG-DArg-Arg-Pro-Ryp-Gly-Igl-Ser-DIgl-Oic-Arg | >20 | 8.1 | |
| B10088 | DArg-Arg-Pro-Hyp-Gly-Igl-Ser-DIgl-Oic-Arg-Eac-Eac-DArg-Arg-Pro-Hyp-Gly-Igl-Ser-DIgl-Oic-Arg | 4 | 7.1 | |
| B10092 | (Gun)$_2$-BApG-DArg-Arg-Pro-Hyp-Gly-Igl-Ser-DIgl-Oic-Arg | >20 | 8.7 | |
| B10098 | (DArg-Arg-Pro-Hyp)$_2$-Dpr-Igl-Ser-DIgl-Oic-Arg | 20 | 5.3 | |
| B10100-2 | TDIM-(DArg-Arg-Pro-Hyp-Gly-Igl-Ser-DIgl-Oic-Arg)$_2$ | 1 | 8.0 | |
| B10100-1 | Moti-DArg-Arg-Pro-Hyp-Gly-Igl-Ser-DIgl-Oic-Arg | 4 | 7.8 | |
| B10104-2 | TDIM-(DArg-Arg-Pro-Hyp-Gly-Thi-Ser-DIgl-Oic-Arg)$_2$ | 4 | 8.0 | |
| B10104-3 | Moti-Darg-Arg-Pro-Hyp-Gly-Thi-Ser-DIGl-Oic-Arg | 20 | 8.1 | |
| B10160 | Leu-DTrp-Phe-DTrp-DNMF-Eac$_2$-DArg-Arg-Pro-Hyp-Gly-Igl-Ser-DIgl-Oic-Arg | 10 | 6.3 | |
| B10162 | Leu-Leu-DTrp-Phe-DTrp-DNMF-Eac$_2$-DArg-Arg-Pro-Ryp-Gly-Igl-Ser-Digl-Oic-Arg | 7 | 6.3 | |
| B10198-1 | DDD-(Eac-Arg-Digl-Oic-Arg)$_2$ | — | 5.7 | |
| B10198-2 | DDD-(Eac-Arg-Digl-Oic-Arg)$_2$ | 15 | — | |
| B10200 | DDD-(Eac-Eac-Arg-DIgl-Oic-Arg)$_2$ | 16 | 5.8 | |
| B10238 | F5c-DArg-Arg-Pro-Hyp-Gly-Igl-Ser-DIgI-Oic-Arg | 150 | 8.1 | |
| B10252 | EGS-(DArg-Arg-Pro-Hyp-Gly-Igl-Ser-DIgl-Oic-Arg)$_2$ | 25 | 8.3 | |
| B10282 | Arg-Pro-Pro-Gly-Phe-Thr-DTic-Oic-Arg | — | 7.3 | |
| B10284 | Arg-Pro-Pro-Gly-Phe-Thr-DTic-Oic-NH$_2$ | — | 7.7 | |
| B10382 | DArg-PzO-Pro-Hyp-Gly-Igl-Ser-DF5F-Oic-Arg | — | — | |
| B10384 | DNiK-PzO-Pro-Hyp-Gly-Igl-Ser-DF5F-Oic-Arg | — | — | |
| B10386 | DDD-(DmK-PzO-Pro-Hyp-Gly-Igl-Ser-DF5F-Oic-Arg)$_2$ | — | — | |
| B10388 | DNiK-PzO-Pro-Hyp-Gly-Igl-Ser-DF5F-Oic-Arg | — | — | |
| B10390 | DNiK-PzO-Pro-Hyp-Gly-Igl-Ser-DIgl-Oic-Arg | — | — | |
| B10392 | DArg-Arg-Pro-Hyp-Gly-Igl-Ser-DIgl-PFF-Arg | — | — | |
| B10394 | F5c-DArg-Arg-Pro-Hyp-Gly-Igl-Ser-DF5F-PFF-Arg | — | — | |
| B10396 | F5c-DArg-Arg-Pro-Hyp-Gly-Igl-Ser-DIgl-PFF-Arg | — | — | |

TABLE 1-continued
ACTIVITIES OF PEPTIDES RELATED TO BRADYKININ STRUCTURE

| NUMBER | STRUCTURE | MTT[a] | GPI[b] | HUMAN[c] |
|---|---|---|---|---|
| M2 | Dcg-D-2-Nal-Arg | — | — | |
| M10 | Dcg-2Nal-Arg | — | 4.8 | |
| M20 | Gun-2-Nal-Arg | — | 4.6 | |
| M42 | Gun-Eac-DIgl-Oic-Arg | — | 5.0 | |
| M68 | Dcg-BtA-Arg | — | 4.9 | |
| M70 | Dcg-Igl-Arg | — | 4.8 | |
| M78 | Dcg-Apa-Arg | — | 5.6 | |
| M84 | Dcg-Ile-Arg | — | 5.1 | |
| M86 | Dcg-Ac6c-Arg | — | 5.0 | |
| M88 | Gun-Ica-Arg | — | 4.7 | |
| M94 | Dcg-Aic-Arg | — | Wk | |
| M96 | Dcg-(D,L)Atc-Arg | — | 4.7 | |
| M118-1 | Ac-PaF(Mcg)-Arg | — | 4.9 | |
| M118-3 | Ac-PdF-Arg | — | 5.4 | |
| M124 | Dcg-Gly-Cmp-Arg | — | 4.7 | |
| M128 | Dcg-Gly-Oic-Arg | — | Wk | |
| M130 | Dcg-F5F-Arg | 20 | 4.8 | |
| M132 | F5bz-F5F-Arg | 60 | Wk | |
| M134 | Dcg-Trx-Arg | — | 4.9 | |
| M142 | Ac-PaF(Sin)-Arg | — | Wk | |
| M146-1 | Ac-PaF(Mcg)-p-ABz-Arg | — | Inact | |
| M146-2 | Ac-PaF(Dcg)-p-ABz-Arg | — | 4.9 | |
| M148 | F5c-p-ABz-Arg | — | 5.1 | |
| M160 | Ste-2-Nal-Arg | — | Wk | |
| M176 | F5c-pABz-2Nal-Arg | Inact | 5.4 | — |
| M196 | FSc-Gly-mABz-2Nal-Arg | Inact | 5.1 | — |
| M198 | Ac-Pac-Gly-m-Abz-2-Nal-Arg | — | 5.1 | |
| M200-1 | Mcg-Pac-Gly-m-ABz-2-Nal-Arg | — | Inact | |
| M200-2 | Dcg-Pac-Gly-m-ABz-2-Nal-Arg | — | 4.9 | |
| M216 | FSc-p-APa-Arg | >180 | | |
| M226 | DDD-(Arg-DIgl-Oic-Arg)$_2$ | 35 | 5.7 | Inact |
| M232-1 | Dcg-Atpc-Arg | — | 4.7 | |
| M232-3 | Dcg-2-Nal-Atpc-Arg | — | 5.1 | |
| M346 | Dcg-p-Amb-Arg | — | 4.6 | |
| M348 | F5c-p-Amb-Arg | — | 4.7 | |
| M352 | F5c-p-Amb-APa-Arg | — | 4.7 | |
| M370 | F5c-Arg | — | 4.8 | |
| M372 | F5c-APb-Arg | — | 4.6 | |
| M374 | Tfmc-Arg | — | 4.6 | |
| M380 | F5c-Tyr-Arg | — | Inact | |
| M382 | F5c-Tic-Arg | — | 4.7 | |
| M388 | F5c-Lys{(CH$_3$)$_3$}-Arg | — | 4.9 | |
| M392 | F5c-Ana-Arg | — | 4.5 | |
| M394 | F5c-Bip-Arg | — | 4.7 | |
| M398 | F5c-Pac-Arg | — | Inact | |
| M400 | DDD-(pABz-2Nal-Arg)$_2$ | 22 | 5.1 | 11.5 |
| M406 | Arg-Eac-DIgl-Ana-Arg | — | Inact | |
| M410 | F5c-Phe-Arg | — | 5.4 | |
| M412 | F5c-m-APa-Arg | — | 5.8 | |
| M416 | F5c-3-Pal-Arg | — | Wk | |
| M420 | F5c-hPhe-Arg | 60 | 7.0 | 10.1 |
| M424 | F5c-Thi-Arg | — | 4.6 | |
| M426 | F5c-Trp-Arg | — | Inact | |
| M442 | F5c-Oic-Arg | — | — | |
| M446 | F5c-2Nal-Arg | 60 | 4.7 | 9 |
| M450 | F5c-2Nal-Arg-NH$_2$ | 26 | 4.9 | Inact |
| M484 | DDD-(Pac-2Nal-Arg)$_2$ | 25 | Inact | Inact |
| M494 | DDD-(Lys-Pac-Gly-mABz-2Nal-NH$_2$)$_2$ | 33 | 5.1 | Inact |
| M498 | DDD-(Pac-2Nal-Arg-NH$_2$)$_2$ | 24 | 4.9 | Inact |
| M500 | DDD-(pABz-2Nal-Arg-NH$_2$)$_2$ | 40 | 0 | 11.4 |
| M504 | DDD-(Pac-2Nal-DArg-NH$_2$)$_2$ | 11 | 5.4 | Wk |
| M508 | DDD-(DArg-2Nal-Arg)$_2$ | 23 | Inact | — |
| M510 | DDD-(DArg-2Nal-Arg-NH$_2$)$_2$ | 8 | Inact | 11 |
| M512 | F5c-OC2Y-Arg | 70 | 5.7 | 11 |
| M516 | DDD-(DArg-Arg-Aud-Pac-2Nal-Arg)$_2$ | 1.4 | 0 | Ag |
| M518 | DDD-(DArg-OC2Y-Arg)$_2$ | 15 | Wk | 10 |
| M520 | F5c-OBS-Arg | Inact | 6.1 | 7 |
| M528 | F5c-MBC-Arg | Inact | Inact | |
| M540 | Pya-hPhe-Arg | >100 | Wk | |
| M542 | Dca-hPhe-Arg | 80 | Wk | |
| M550 | F5c-OBT-Arg | 80 | Inact | Ag |
| M552 | DDD-(p-ABz-hPhe-Arg)$_2$ | Inact | Inact | |
| M554 | DDD-(DArg-hPhe-Arg)$_2$ | — | 5.1 | |
| M558 | Dcg-hPhe-Arg | 100 | Wk | |
| M560 | DDD-(DArg-hPhe-Arg-NH$_2$)$_2$ | 50 | Wk | |

TABLE 1-continued

ACTIVITIES OF PEPTIDES RELATED TO BRADYKININ STRUCTURE

| NUMBER | STRUCTURE | MTT[a] | GPI[b] | HUMAN[c] |
|---|---|---|---|---|
| M564 | DDD-(DArg-OBS-Arg)$_2$ | — | Wk | |
| M590 | Atmp-Igl-Pac-α-Sbl-Lys-B9430 | 4.5 | 7.5 | Inact |
| M598 | DDD-(Arg-DIgl-Oic-Arg-OMe)$_2$ | 13 | — | 10 |
| M600 | α-DDD-(Lys-B9430-OMe)$_2$ | 1.2 | 6.4 | Ag |
| M608 | DDD-(Eac-Arg-DIgl-Oic-Arg-OMe)$_2$ | 13 | — | Inact |
| M612 | F5c-DArg-hPhe-Arg | Inact | Wk | |
| M676 | DDD-(DArg-Arg-Eac-Ser-DF5F-Nc7G-Arg)$_2$ | — | — | |
| M682 | F5c-Lys(F5bz)-Arg | — | 4.9 | |
| M686 | F5c-NMF-Arg | 29 | 5.6 | |
| M688 | F5c-Dpr(Fbz)-Arg | — | Inact | |
| M690 | F5c-Dpr(Paa)-Arg | — | 4.8 | |
| M692 | DDD-(DArg-Arg-Aud-Pac-hPhe-Arg)$_2$ | — | Wk | |
| M696 | F5c-DArg-Eac-2Nal-Arg | Inact | 5.1 | — |
| M698 | F5c-DArg-Arg-Aud-Pac-2Nal-Arg | 7.1 | Wk | — |
| M706 | Cin-hPhe-Arg | Inact | Wk | |
| M708 | Ppa-hPhe-Arg | Inact | 5.8 | |
| M710 | DDD-(DArg-Arg-Aud-Pac-2Nal-DArg-NH$_2$)$_2$ | 1.7 | Wk | |
| M714 | F5c-PCF-Arg | Inact | Wk | |
| M718 | F5c-PFF-Arg | 9 | 5.1 | |
| M720 | F5c-PaF(Ppa)-Arg | Inact | 4.8 | |
| M726 | D-Arg-Arg-Aud-PaF(F5c)-Arg | Inact | 5.6 | |
| M728 | DDD-(DArg-Arg-Aud-PaF(F5c)-Arg)$_2$ | 4 | 5.3 | |
| M730 | F5c-DhPhe-Arg | — | 4.7 | |
| M732 | F5c-PNF-Arg | — | 4.9 | |
| M734 | DDD-(DArg-Arg-Aud-Pac-PaF(Fbz)-Arg)$_2$ | 1.8 | 5.3 | |
| M738 | F5c-DArg-Eac-hPhe-Arg | Inact | 5.3 | |
| M746 | DDD-(Pac-hPhe-Arg)$_2$ | Inact | Inact | |
| M752-2 | Pac-hPhe-Arg | Inact | Wk | |
| M752-5 | Aaa-Ser-Pac-hPhe-Arg | Inact | Wk | |
| M752-6 | Aaa-Pac-hPhe-Arg | Inact | Wk | |
| M754 | Aaa-DPhe-hPhe-Arg | Inact | 4.6 | |
| M756 | DDD-(DPhe-hPhe-Arg)$_2$ | 18 | 5.2 | |
| M758 | Saa-hPhe-Arg | — | Wk | |
| M764 | Aaa-DTic-hPhe-Arg | — | 4.8 | |
| M766 | F5c-DArg-Arg-Aud-DTic-hPhe-Arg | — | 5.1 | |
| M770 | DDD-(DArg-Arg-Aud-DTic-hPhe-Arg)$_2$ | 8 | Inact | |
| M772 | Aaa-DIgl-hPhe-Arg | — | 4.9 | |
| M774 | F5c-DArg-Arg-Aud-DIgl-hPhe-Arg | 8 | Inact | |
| M776 | DDD-(DIgl-hPhe-Arg)$_2$ | 30 | 5 | |
| M778-1 | Pcc-hPhe-Arg | — | Wk | |
| M780 | Mca-hPhe-Arg | — | Wk | |
| M782 | Cca-hPhe-Arg | — | Wk | |
| M784 | Ac-OC2Y-Arg | Inact | Wk | |
| M786 | DDD-(DArg-Arg-Aud-DIgl-hPhe-Arg)$_2$ | 3.2 | Wk | |
| M788 | F5c-DArg-Arg-Aud-DTic-Oic-Arg | 9 | 5 | |
| M790 | DDD-(DArg-Arg-Aud-DTic-Oic-Arg)$_2$ | 1.7 | Inact | |
| M792 | F5c-DArg-Arg-Eac-Ser-DTic-Oic-Arg | >100 | 4.9 | |
| M794 | DDD-(DArg-Arg-Eac-Ser-DTic-Oic-Arg)$_2$ | 21 | Inact | |
| M796 | F5c-DArg-Arg-Eac-Ser-DF5F-Oic-Arg | 31 | 6.5 | |
| M802 | F5c-Lys-Ser-DF5F-Oic-Arg | Inact | 6.3 | |
| M804 | DDD-(DArg-Arg-Eac-Ser-DF5F-Oic-Arg)$_2$ | 7.3 | 7.7 | |
| M806 | Ava-Igl-Ser-DF5F-Oic-Arg | Inact | 5.6 | |
| M808 | DDD-(Lys-Ser-DF5F-Oic-Arg)$_2$ | 30 | 6.9 | |
| M810 | F5c-F5F-Arg | 40 | 4.6 | |
| M812 | F5c-PFF-Arg-NH$_2$ | 15 | Wk | |
| M814 | Ppa-PFF-Arg | Inact | Wk | |
| M816 | Dpa-PFF-Arg | 52 | 4.6 | |
| M818 | DDD-(DArg-PFF-Arg-NH$_2$)$_2$ | 60 | Wk | |
| M820 | DDD-(DArg-PFF-Arg)$_2$ | 43 | Inact | |
| M822 | DDD-(DArg-F5F-Arg)$_2$ | 25 | Mixed | |
| M826 | F5c-MFF-Arg | 76 | Inact | |
| M828 | F5c-3,4F2F-Arg | — | Wk | |
| M838 | F5c-DArg-Arg-Aud-DIgl-PFF-Arg | 7.4 | 5.1 | |
| M842 | DDD-(DArg-Arg-Aud-DIgl-PFF-Arg)$_2$ | 1.4 | Inact | |
| M844 | DArg-Arg-Aud-DIgl-PFF-Arg | 12 | Wk | |
| M846 | DDD-(DArg-Arg-Aud-DF5F-Oic-Arg)$_2$ | 2 | 7.1 | |
| M852 | F5c-DArg-Arg-Eac-Ser-DIgl-Oic-Arg | Inact | 5.9 | |
| M854 | DDD-(DArg-Arg-Eac-Ser-DIgl-Oic-Arg)$_2$ | 7.3 | 5.9 | |
| M856 | F5c-DArg-Arg-Aud-Ser-DIgl-Oic-Arg | 21 | 5.4 | |
| M858 | DDD-(DArg-Arg-Aud-Ser-DIgl-Oic-Arg)$_2$ | 4 | 6.3 | |
| M860 | F5c-DArg-Arg-Add-Ser-DIgl-Oic-Arg | 6 | 5.4 | |
| M862 | DDD-(DArg-Arg-Add-Ser-DIgl-Oic-Arg)$_2$ | 1.3 | 5.6 | |
| M864 | DDD-(DArg-Arg-Add-Ser-DIgl-PFF-Arg)$_2$ | 1.8 | Inact | |
| M868 | Ac-Darg-Arg-Aud-DF5F-Oic-Arg | 55 | 6.5 | |
| M888 | F5c-DArg-Arg-Aud-Ser-DF5F-Oic-Arg | 12.5 | 6.6 | |

TABLE 1-continued

ACTIVITIES OF PEPTIDES RELATED TO BRADYKININ STRUCTURE

| NUMBER | STRUCTURE | MTT[a] | GPI[b] | HUMAN[c] |
|---|---|---|---|---|
| M890 | DDD-(DArg-Arg-Aud-Ser-DF5F-Oic-Arg)$_2$ | 1.7 | 5.5 | |
| M922 | DDD-(DNiK-Arg-Eac-Ser-DF5F-Oic-Arg)$_2$ | — | — | |
| M926 | ζ-SUB-(ApC-F5F-Arg)$_2$ | Inact | — | |
| M930 | α-DDD-(ApC-F5F-Arg)$_2$ | Inact | — | |
| M932 | DDD-(DArg-Arg-Eac-Ser-DIgl-PFF-Arg)$_2$ | 6.0 | — | |
| M936 | DDD-(DNiK-PzO-Eac-Ser-DF5F-Oic-Arg)$_2$ | — | — | |
| M944 | DDD-(DArg-Arg-Eac-Ser-DF5F-PFF-Arg)$_2$ | 6.7 | — | |
| M946 | F5c-DArg-Arg-Eac-Ser-DF5F-PFF-Arg | — | — | |
| M950 | α-DDD-(K-DArg-Arg-Eac-Ser-DF5F-Oic-Arg)$_2$ | 6.7 | — | |
| M952 | DDD-(DmK-DArg-Arg-Eac-Ser-DF5F-Oic-Arg)$_2$ | — | — | |
| M954 | Aaa-DArg-Arg-Eac-Ser-DF5F-Oic-Arg | 10 | — | |
| M956 | Aaa-DArg-Arg-Aud-Ser-DF5F-Oic-Arg | 14 | — | |
| M958 | F5bz-DArg-Arg-Aud-Ser-DF5F-Oic-Arg | 18 | — | |
| M960 | Aca-DArg-Arg-Aud-Ser-DF5F-Oic-Arg | 21 | — | |
| M964 | 33Dp-DArg-Arg-Aud-Ser-DF5F-Oic-Arg | 4–8 | — | |
| M968 | Dmac-DArg-Arg-Aud-Ser-DF5F-Oic-Arg | 15 | — | |
| M972 | F5pa-DArg-Arg-Aud-Ser-DF5F-Oic-Arg | — | — | |
| M974 | DDD-(PzO-F5F-Arg)$_2$ | — | — | |
| M976 | DDD-(DNiK-F5F-Arg)$_2$ | — | — | |
| M978 | DDD-(DPzK-F5F-Arg)$_2$ | — | — | |
| M980 | DDD-(DPzO-F5F-Arg)$_2$ | — | — | |
| M1024 | SUB-(DArg-Arg-Eac-Ser-DF5f-Nc7G-Arg)$_2$ | 14 | 7.2 | |
| M1026 | DTP-(DArg-Arg-Eac-Ser-DF5F-Nc7G-Arg)$_2$ | 70 | 6.9 | |
| M1028 | SBEC-(DArg-Arg-Eac-Ser-DF5F-Nc7G-Arg)$_2$ | 28 | 6.7 | |
| M1030 | EGS-(DArg-Arg-Eac-Ser-DF5F-Nc7G-Arg)$_2$ | 51 | 7.0 | |
| M1034 | DDD-(DArg-F5F-DArg-NH$_2$)$_2$ | — | — | |
| M1036 | DDD-(DArg-F5F-DArg)$_2$ | 40 | 5.4 | |
| M1038 | ε-SUB-(Lys-DArg-Arg-Eac-Ser-DF5F-Nc7G-Arg)$_2$ | — | 6.4 | |
| M1042 | Aca-DArg-Arg-Eac-Ser-DF5F-Oic-Arg | — | — | |
| M1044 | Gun$_2$-BApg-DArg-Arg-Eac-Ser-DF5F-Oic-Arg | — | — | |
| M1046 | (F5c-DArg-Igl-Arg)$_2$-DDA | — | — | |

Footnotes:
[a]ED$_{50}$ for killing of SCLC strain SHP-77 in vitro, μM.
[b]pA$_2$ for bradykinin antagonist activity on isolated guinea pig ileum. The pD$_2$ of bradykinin is 7.4 on ileum. Higher numbers indicate higher potency.
[c]pA$_2$ for bradykinin antagonist potency on cloned human B2 receptors, pM. The pD$_2$ for bradykinin is 11. Higher numbers indicate higher potency.
[d]Data included for comparison
Inact = inactive; Mixed = showing both agonist and antagonist activity; Wk = weak

TABLE 2

ACTIVITIES OF COMPOUNDS NOT RELATED TO BRADYKININ

| NUMBER | STRUCTURE | MTT[a] | GPI[b] | HUMAN[c] |
|---|---|---|---|---|
| B9948 | Arg-DNMF-DTrp-Phe-DTrp-Leu | 2.8 | Wk | |
| B10222 | DNMF-DTrp-Phe-DTrp-LeuΨ(CH$_2$NH)Leu-NH$_2$ | 6.0 | 5.2 | |
| B10224-1 | α-DDD-(Lys-DNMF-DTrp-Phe-DTrp-LeuΨ(CH$_2$NH)Leu-NH$_2$)$_2$ | 13 | — | |
| B10224-2 | α-DDD-(Lys-DNMF-DTrp-Phe-DTrp-LeuΨ(CH$_2$NH)Leu-NH$_2$)$_2$ | 7 | — | |
| B10228 | DDD-(DNMF-DTrp-Phe-DTrp-LeuΨ(CH$_2$NH)Leu-NH$_2$)$_2$ | 40 | Wk | |
| B10242 | Arg-Pro-Lys-Pro-DTrp-Gln-DTrp-Phe-DTrp-LeuΨ(CH$_2$NH)Leu-NH$_2$ | 40 | 5.6 | |
| B10244 | DArg-Arg-Pro-Lys-Pro-DTrp-Gln-DTrp-Phe-DTrp-LeuΨ(CH$_2$NH)Leu-NH$_2$ | 12 | 5.4 | |
| B10246 | DArg-Pro-Lys-Pro-DTrp-Gln-DTrp-Phe-DTrp-LeuΨ(CH$_2$NH)Leu-NH$_2$ | 12 | 6.1 | |
| >278 | F5c-Iqa-Atmp | 9 | 5.3 | — |
| M8 | Gun-Eac-D2Nal-PgF | — | Inact | |
| M12 | Dcg-Igl-Aqu | 20 | 5.0 | — |
| M18 | Dcg-2Nal-Aqu | 30 | 6.6 | — |
| M26 | Gun-2Nal-GaP | — | 4.9 | |
| M30 | Dcg-2Nal-Apa | — | 5.4 | |
| M32 | Gun-2Nal-Apa | — | 4.8 | |
| M36 | Dcg-D2Nal-Apa | — | 5.0 | |
| M38 | Gun-D2Nal-Apa | — | 4.9 | |
| M62 | Dcg-2Nal-Ama | — | 4.8 | |
| M64 | Dcg-2Nal-APa-Sud | — | Ag | |
| M72-1 | Dcg-Igl-Apa | — | 4.7 | |
| M72-2 | Dcg-Igl-APa(anisyl) | — | 4.6 | |

TABLE 2-continued

ACTIVITIES OF COMPOUNDS NOT RELATED TO BRADYKININ

| NUMBER | STRUCTURE | MTT[a] | GPI[b] | HUMAN[c] |
|---|---|---|---|---|
| M76 | Dcg-2Nal-mABz | — | 4.9 | |
| M92-1 | Dcg-2Nal-mA$_2$Bz | — | 5.0 | |
| M92-2 | Dcg-2Nal-mA$_2$Bz(Gun) | — | 4.8 | |
| M92-4 | Dcg-2Nal-3Pal | — | 5.0 | |
| M104 | Dcg-2Nal-3Pal | — | 4.9 | |
| M112 | Dcg-D2Nal-mABz | — | 5.1 | |
| M120 | Dcg-2Nal-pABz | — | 4.7 | |
| M122-1 | Mcg-APa-mABz | — | 5.0 | |
| M122-2 | Dcg-Apa-mABz | — | 4.6 | |
| M136 | Sin-F5F-3Pal | — | Inact | |
| M162 | Dcg-2Nasl-Asp | — | 4.9 | |
| M168-1 | 2Nap-PaF(Mcg) | — | 4.8 | |
| M168-2 | 2Nap-PaF(Dcg) | — | 4.7 | |
| M172 | Inp-Dpr(Dcg-2Nal) | — | 4.9 | |
| M174 | Dcg-Asp-Aqu | — | Inact | |
| M180 | F5c-pABz-2Nal | — | 5.1 | |
| M188B | Dcg-2Nal-Asp(Aqu) | — | 5.5 | |
| M202 | F5c-Gly-mABz-Nal | — | 5.1 | |
| M204 | Ac-Pac-Gly-mABz-Nal | — | 5.0 | |
| M218 | 2Nal-Atmp | Inact | 4.8 | |
| M222 | Dcg-2Nal-Atmp | 15 | 6.8 | Inact |
| M228-2 | Dcg(Me)-2Nal-Atmp(Me) | 15 | 7.6 | — |
| M236 | Dcg-Igl-Atmp | >50 | 4.7 | — |
| M240 | Dcg-F5f-Atmp | 32 | 5.1 | — |
| M244A | Dcg-2Nal-Atpm | 12 | 5.0 | |
| M244B | Dcg-2Nal-Atpc | Inact | 4.9 | |
| M246 | Dcg-D2Nal-Atmp | >50 | 5.7 | |
| M248 | F5c-2Nal-Atmp | 3.2 | 6.2 | — |
| M250 | Aca-2Nal-Atmp | — | 5.2 | |
| M252 | Dhq-2Nal-Atmp | Inact | 4.8 | |
| M254 | TDIM-(2Nal-Atmp)$_2$ | 5 | 5.1 | — |
| M254-1 | TDIM-(2Nal-Atmp)$_2$ | 5 | 5.1 | |
| M254-2 | TDIM-(2Nal-Atmp)$_2$ | 5 | 5.8 | |
| M258 | Dcg-Igl-Aptp | — | 5.0 | |
| M262 | Dcg-D2Nal-Atmp | 6 | 5.3 | |
| M264 | Dcg-Trp-Atmp | 16 | 4.7 | — |
| M266 | Dcg-Apa-Atmp | 42 | 4.8 | — |
| M268 | F5c-2Nal-Tpac | 10 | 5.2 | — |
| M270 | Dcg-2Nal-Tpac | — | 6.1 | |
| M272 | Dpa-2Nal-Atmp | 9 | 5.2 | — |
| M274 | Sin-2Nal-Atmp | 36 | 4.7 | — |
| M276 | Dca-2Nal-Atmp | 4.6 | 5.3 | — |
| M280 | TDIM-(Igl-Atmp)2 | 6 | 5.2 | — |
| M280-1 | Ctim-Igl-Atmp | 21 | Wk | |
| M280-2 | TDIM-(Igl-Atmp)$_2$ | 6 | 5.2 | |
| M286 | Dtp-(2Nal-Atmp)$_2$ | 24 | 5.1 | — |
| M288 | Boc-2Nal-Atmp | Inact | 5.2 | — |
| M288A | Boc-2Nal-Atmp | >85 | 5.2 | |
| M290-1 | Btac-(2Nal-Atmp)$_2$ | >60 | Wk | |
| M290-2 | Btac-(2Nal-Atmp)$_3$ | 20 | Wk | |
| M292 | Pac-Igl-Atmp | 40 | Wk | |
| M294 | DDD-(Pac-Igl-Atmp)$_2$ | 1.8 | Inact | 10.3 |
| M296 | Pya-Bip-Atmp | 15 | Wk | |
| M302 | Atcp-2Nal-Atmp | 3.5 | 5.2 | |
| M304 | TDIM-(2Nal-Dmm)$_2$ | 4.2 | 5.9 | — |
| M306 | Gbz-2Nal-Atmp | >100 | — | |
| M308 | Pac-2Nal-Atmp | >75 | 5.0 | |
| M310 | DDD-(Pac-2Nal-Atmp)$_2$ | 1.2 | 5.1 | Inact |
| M312 | Tfmc-2Nal-Atmp | 3.2 | 5.5 | — |
| M314 | F5c-2Nal-Aqd | 25 | 4.6 | |
| M316 | F5c-Tyr-Atmp | 50 | — | |
| M318 | F5c-Tyr(Bzl)-Atmp | 3.6 | 5.1 | — |
| M320 | F5c-Oic-Atmp | 13 | — | — |
| M322 | F5c-Tic-Atmp | 7.6 | — | — |
| M324 | Dmac-2Nal-Atmp | 3 | 5.2 | — |
| M336-1 | Dcg-2Nal-Asp-(R,S)Aqu | — | 5.1 | |
| M336-2 | Dcg-2Nal-Asp-(R,S)Aqu | — | 5.4 | |
| M340 | Dcg-Pac-Gly-mABz-2Nal | — | 4.8 | |
| M342 | Dcg-2Nal-Asp-Atmp | — | 5.4 | |
| M350 | Dcg-2Nal-Glu-Atmp | — | 5.0 | |
| M354 | Dcg-2Nal-PgF | — | 5.2 | |
| M362 | Dcg-pAPa-Asp-Atmp | — | 4.9 | |
| M364 | F5c-pAPa-Asp-Atmp | — | 4.7 | |
| M368 | Tfmc-pAPa-Asp-Atmp | — | 4.7 | |
| M396 | F5c-2Nal-Cys(SO$_3$H)-Atmp | — | 5.0 | |

TABLE 2-continued

ACTIVITIES OF COMPOUNDS NOT RELATED TO BRADYKININ

| NUMBER | STRUCTURE | MTT[a] | GPI[b] | HUMAN[c] |
|---|---|---|---|---|
| M408 | Pya-2Nal-Cyh | 22 | 4.6 | 11.5 |
| M418 | F5c-BtA-Atmp | 3.8 | 7.0 | 10.3 |
| M422 | Pya-pABz-2Nal | 52 | — | Inact |
| M428 | Pya-Gly-mABz-Aqd | >300 | — | |
| M430 | DDD-(BtA-Atmp)$_2$ | 18 | 5.3 | 11.3 |
| M432 | DDD-(2Nal-Asp-Atmp)$_2$ | 70 | — | 10 |
| M436-1 | TDIM-BtA-Atmp | 8 | 4.8 | |
| M436-2 | TDIM-(BtA-Atmp)$_2$ | 4.5 | 5.8 | Ag |
| M438 | F5c-3Pal-Atmp | 26 | 4.8 | 10 |
| M440 | Dcg-BtA-Atmp | 30 | — | |
| M448 | Dmac-BtA-Atmp | 2.7 | 5.7 | Ag |
| M456 | F5c-Cys(Meb)-Atmp | 4.7 | 5.3 | Inact |
| M460 | DDD-(3Pal-Nal-Cyh)$_2$ | 15 | Wk | |
| M466 | F5c-2Nal-3Ampy | Inact | Wk | |
| M470 | F5c-2Nal-Ampz | 11 | 5.2 | Inact |
| M472 | Dmac-2Nal-Ampz | 25 | 5.3 | Inact |
| M474 | Pya-2Nal-3Abza | 35 | Wk | Inact |
| M476 | Tha-BtA-Atmp | 15 | 4.6 | Inact |
| M478 | Dmac-2Nal-Thm | 30 | 5.1 | Inact |
| M480-1 | HOOC-DDD-Pac-2Nal-Ampz | 45 | 5.1 | |
| M480-2 | DDD-(Pac-2Nal-Ampz)$_2$ | — | 5.6 | |
| M492 | F5c-mABz-2Nal-Ampz | 45 | 5.1 | Inact |
| M506 | Mse-Pac-BtA-Atmp | 11 | 4.9 | — |
| M526 | F5c-2Nal-Dmp | 10 | 5.4 | |
| M536 | F5c-2Nal-Dmab | 4 | Wk | Inact |
| M538 | DDD-(Pac-2-Nal-Dmp)$_2$ | >80 | Wk | |
| M568 | F5po-2Nal-Atmp | 10 | 5.8 | Ag |
| M570 | F5c-OC2Y-Atmp | 1.8 | 5.6 | Ag |
| M572 | Dca-2Nal-Acep | 2.6 | Wk | Wk |
| M574 | Dns-Tyr(Bzl)Atmp | 4.5 | — | Inact |
| M582 | Dmac-OC2Y-Atmp | 3 | 5.4 | 9.5 |
| M584-A | DDD-[DArg(Tos)-2Nal-Atmp]$_2$ | 5 | Inact | 10.3 |
| M584-B | DDD-(DArg-2Nal-Atmp)$_2$ | 5 | 5.7 | 11.3 |
| M586-A | Mse-Pac-Igl-Atmp | 15 | 5.3 | 12 |
| M586-B | Seb-Pac-Igl-Atmp | 40 | Wk | 12.3 |
| M588 | α-DDD-(Lys-DArg-2Nal-Atmp)$_2$ | 9.4 | Wk | 10 |
| M592 | F5c-OC2Y-Matp | 1.5 | 4.9 | Ag |
| M594 | F5c-MC2Y-Atmp | 3.7 | 5.0 | 8 |
| M594 | F5c-MC2Y-Atmp | 3.7 | 5.0 | 8 |
| M596-A | DDD-[Arg(Tos)-2Nal-Atmp]$_2$ | 8.2 | Wk | Inact |
| M596-B | DDD-(Arg-2Nal-Atmp)$_2$ | 8.2 | Wk | Inact |
| M602 | Chc-OC2Y-Atmp | 12 | — | 10.8 |
| M604 | Pac-2Nal-Ecap | 43 | 4.5 | |
| M606 | DDD-(Pac-2Nal-Api)$_2$ | 30 | 5.0 | 10 |
| M614 | F5c-(N-Dmb)-Tyr(Bzl)-OMe | 9.1 | Wk | |
| M616 | DDD-(Pac-1Nal-Atmp)$_2$ | 1.4 | 5.4 | — |
| M618 | F5c-DArg-2Nal-Arg-Matp | 18 | — | — |
| M620 | DDD-(DArg-2Nal-Arg-Matp)$_2$ | 2.0 | 5.5 | — |
| M622 | F5c-OC2Y-Mapp | 1.2 | 5.7 | — |
| M624 | Dns-OC2Y-Matp | 1.4 | 5.1 | — |
| M626 | Pya-OC2Y-Matp | 3.7 | 4.8 | — |
| M628 | Cin-OC2Y-Matp | 1.6 | 5.2 | — |
| M630 | Dmac-OC2Y-Matp | 1.6 | 5.0 | — |
| M632 | Atcp-OC2Y-Matp | 1.4 | 5.4 | — |
| M636 | DDD-(DArg-Arg-Aud-Pac-2Nal-Atmp)$_2$ | 1.7 | 5.8 | — |
| M638 | DDD-(DArg-Igl-Arg-Matp)$_2$ | 0.6 | Inact | |
| M640 | DDD-(DArg-BtA-Arg-Matp)$_2$ | 3.0 | 5.9 | |
| M648 | F5c-PaF(Mes)-Atmp | Inact | 5.0 | |
| M650 | Atcp-OC2Y-Mapp | 3.7 | — | — |
| M652 | Ppa-OC2Y-Mapp | 7.5 | 5.7 | — |
| M654 | Sul-Atmp | Inact | 4.5 | |
| M656 | Sul-2Nal-Atmp | 13 | 5.4 | |
| M660 | DDD-(His-1Nal-Atmp)$_2$ | 30 | Wk | — |
| M662 | F5c-tLeu-Atmp | Inact | 5.2 | — |
| M664 | F5c-OCIY-Matp | 1.2 | 5.0 | |
| M666 | Dns-OCIY-Matp | 1.3 | 5.0 | |
| M668 | SBEC-(DArg-2Nal-Arg-Matp)$_2$ | 3.4 | 5.2 | |
| M670 | DTP-(DArg-Igl-Arg-Matp)$_2$ | Inact | 5.1 | |
| M672 | HDD-(DArg-Igl-Arg-Matp)$_2$ | — | — | |
| M674 | DDD-(DArg-F5F-Arg-Matp)$_2$ | 3.5 | Wk | |
| M678 | (Dns-DArg-Igl-Arg)$_2$-DDA | 1.1 | 5.3 | |
| M724 | F5c-DArg-Aud-OC2Y-Gly-Atmp | 12 | 5.4 | |
| M744 | DDD-(DArg-2Nal-Arg-Dmab)$_2$ | 3.4 | 5.3 | |
| M798 | F5c-OC2Y-Dmab | 37 | — | |
| M800 | DDD-(DArg-OC2Y-Dmab)$_2$ | 27 | 5.3 | |

TABLE 2-continued

ACTIVITIES OF COMPOUNDS NOT RELATED TO BRADYKININ

| NUMBER | STRUCTURE | MTT[a] | GPI[b] | HUMAN[c] |
|---|---|---|---|---|
| M832 | F5c-PFF-Dmab | 47 | 4.6 | |
| M834 | DDD-(DArg-PFF-Arg-Dpea)$_2$ | 1.6 | 5.3 | |
| M848 | DDD-(DArg-F5F-Arg-Dmab)$_2$ | — | — | |
| M880 | DDD-(DArg-F5F-Arg-Dpea)$_2$ | — | — | |
| M886-1 | DDD-DArg-PFF-Arg-NH$_2$ <br>     └—DArg-PFF-Arg-Dpma | 3.2 | Wk | |
| M886-2 | DDD-(DArg-PFF-Arg-Dpma)$_2$ | — | Inact | |
| M892 | DDD-(DArg-PFF-Arg-PFF-NH$_2$)$_2$ | 8.5 | Wk | |
| M900 | DDD-(DArg-F5F-Arg-PaF-NH$_2$)$_2$ | 6.3 | — | |
| M916 | F5c-DArg-PFF-Arg-PFF-NH$_2$ | 5.7 | 4.9 | |
| M1032 | DDD-(DArg-Igl-Mapp)$_2$ | 15 | 5.4 | |
| M1040 | EDTA-(OC2Y-Atmp)$_4$ | 0.73 | — | |

Footnotes:
[a]ED$_{50}$ for killing of SCLC strain SHP-77 in vitro, μM.
[b]pA$_2$ for bradykinin antagonist activity on isolated guinea pig ileum. The pD$_2$ of bradykinin is 7.4 on ileum. Higher numbers indicate higher potency.
[c]pA$_2$ for bradykinin antagonist potency on cloned human B2 receptors, pM. The pD$_2$ for bradykinin is 11. Higher numbers indicate higher potency.
Ag = agonist; Inact = inactive; Wk = weak

TABLE 3

ACTIVITIES OF CYCLIC PEPTIDES

| NUMBER | STRUCTURE | MTT[a] | GPI[b] |
|---|---|---|---|
| B9458-2 | DArg-Arg-Pro-Hyp-GlyThi-Ser-DTic-CpGΨ(CH$_2$N)Arg <br>    └——CO——CH$_2$——/ \ <br> CH$_2$CO$_2$H | — | 6.1 |
| B9462 | Darg-Arg-Pro-Hyp-Gly-Thi-Ser-Digl-CpGΨ(CH$_2$N)Arg <br>    └——CO——CH$_2$——/ \ <br> CH$_2$CO$_2$H | 7.3 | 6.0 |
| B10302 | c[DArg-Arg-Pro-Hyp-Gly-Igl-Ser-DIgl-Oic-Arg] | Inact | 5.2 |
| B10304 | Aca-c[DArg-Arg-Pro-Hyp-Gly-Thi-Ser-Nig-Oic-Arg] | Inact | 6.4 |
| B10306 | c[Arg-DNMF-DTrp-Phe-DTrp-Leu] | Inact | Wk |
| B10312 | α-DDD-(c[Lys-DArg-Arg-Pro-Hyp-Gly-Thi-Ser-DF5F-Oic-Arg])$_2$ | 3.8 | — |
| M680 | c[DArg-Arg-Eac-Ser-DF5F-Nc7G-Arg] | — | — |
| M824 | c[Ava-Igl-Ser-DF5F-Oic-Arg] | Inact | 5.2 |
| M850 | c[DArg-Arg-Aud-DIg1-PFF-Arg] | 1.4 | 5.1 |
| M868-2 | c[DArg-Arg-Aud-DF5F-Oic-Arg] | 9.2 | 6.1 |
| M870 | c[DArg-Arg-Add-DF5F-Oic-Arg] | 5.5 | 5.3 |
| M872 | c[DArg-Arg-Eac-Ser-DF5F-Oic-Arg] | 2.2 | Inact |
| M874 | c[DArg-Arg-Add-Ser-DF5F-Oic-Arg] | 11 | 5.0 |
| M876 | c[DArg-Arg-Aud-Ser-DF5F-Oic-Arg] | 22.5 | 5.4 |
| M878 | c[DArg-Arg Add-DIgl-PFF-Arg] | 7 | Wk |
| M882 | c[DArg-Arg-Add-Ser-DIgl-PFF-Arg] | 4.5 | Inact |
| M896 | c[DArg-Arg-Eac-DIgl-PFF-Arg] | 65 | Wk |
| M902 | c[DArg-Arg-Ava-Ser-DIgl-PFF-Arg] | 30 | 5.5 |
| M906 | c[DArg-Arg-Eac-DF5F-Oic-Arg] | 45 | Wk |
| M908 | c[DArg-Arg-Ava-Ser-DF5F-Oic-Arg] | 40 | 4.9 |
| M910 | c[Bala-DArg-Arg-Eac-Ser-DF5F-Oic-Arg] | 42 | 5.2 |
| M924 | c[Suc-DArg-Arg-Eac-Ser-DIgl-PaF]-Arg | 37 | Wk |
| M934 | c[DNiK-Arg-Eac-Ser-DF5F-Oic-Arg] | — | — |
| M940 | c[DNiK-PzO-Eac-Ser-DF5F-Oic-Arg] | — | — |
| M986 | c[Add-DArg-F$_5$F-Arg] | — | — |

Footnotes:
[a]ED$_{50}$ for killing of SCLC strain SHP-77 in vitro, μM.
[b]pA$_2$ for bradykinin antagonist activity on isolated guinea pig ileum. The pD$_2$ of bradykinin is 7.4 on ileum. Higher numbers indicate higher potency.
Inact = inactive;
Wk = weak

TABLE 4

PREVIOUSLY DESCRIBED KNOWN PEPTIDES THAT NEWLY SHOW IN VIVO ANTI-CANCER ACTIVITY

| NUMBER | STRUCTURE |
|---|---|
| B9430 | DArg—Arg—Pro—Hyp—Gly—Igl—Ser—DIgl—Oic—Arg |
| B9330 | DArg—Arg—Pro—Hyp—Gly—Thi—Ser—DTic—Nig—Arg |
| B10044 | DArg—Arg—Pro—Hyp—Gly—Igl—Ser—DF5F—Oic—Arg |
| B10050 | Lys—Lys—Arg—Pro—Hyp—Gly—Igl—Ser—DTic—ChG |
| B10206 | DArg—Arg—Pro—Hyp—Gly—Igl—Ser—DF5F—Nc7G—Arg |
| B10288 | DArg—Arg—Pro—Hyp—Gly—Thi—Ser—DTic—Oic—Arg |

These compounds showed anti-tumor activity in vivo when tested by the procedure of Example XXI.

TABLE 5

CYTOTOXICITY IN VITRO AGAINST STRAINS OF PROSTATE CANCER

| COMPOUND NUMBER | PROSTATE CANCER CELL LINE | | | | | SCLC SHP-77 |
|---|---|---|---|---|---|---|
| | DU14 | TSU | LNCa | PC-3 | PPC1 | |
| B9870 | 0.08 | 6.5 | 3.7 | 3.2 | 4.3 | 0.15 |
| M570 | 1.2 | 2.8 | 3.0 | 1.6 | 3.0 | 1.8 |
| M590 | 0.01 | 7.0 | 7.0 | 6.3 | 12 | 4.5 |

Numbers are $ED_{50}$ ($\mu$M) for cytotoxic activity. Activity against SCLC strain SHP-77 is included for comparison.

TABLE 6

ABBREVIATIONS USED FOR COMPOUNDS

B9430 = DArg-Arg-Pro-Hyp-Gly-Igl-Ser-DIgl-Oic-Arg
B9870 = SUIM-(DArg-Arg-Pro-Hyp-Gly-Igl-SAer-DIgl-Oic-Arg)$_2$
Aaa = 1-Adamantaneacetyl
AAA = amino acid analysis
ABz = Aminobenzoic acid
ABza = Aminobenzyl alcohol
Ac = Acetyl
Ac3c = 1-Amino-1-cyclopropanecarboxylic acid
Ac5c = 1-Amino-1-cyclopentanecarboxylic acid ("cyclo-Leu")
Ac6c = 1-Aminocyclohexanecarboxylic acid
Aca = 1-Adamantanecarboxyl
Acep = 4-Amino-1-carbethoxymethyl-2,2,6,6-tetramethylpiperidine
ADA = 1,3-Adamantanediacetyl
Add = 12-Aminododecanoic acid
Aib = α-Aminoisobutyric acid
Aic = 2-Aminoindane-2-carboxylic acid
A1G = α-Allylglycine (2-amino-5-pentenoic acid)
Ama = Aminomethylanthranilic acid
Amb = Aminomethylbenzoic acid
Ampy = 3-Aminomethylpyridine
Ampz = 1-Amino-4-methylpiperazine
Ana = Anthranilic acid
APa = p-Aminophenylacetic acid
APb = p-Aminophenylbutyric acid
ApC = S-3-Aminopropylcysteine
Api = 4-Aminopiperidine
Apmp = 4-Amino-1,2,2,6,6-pentamethylpiperidine
Aptp = 4-Amino-1-phenylmethyl-2,2,6,6-tetramethylpiperidine
Aqd = 4-Aminoquinaldine
Aqu = 3-Aminoquinuclidine
Arg(NO$_2$) = Arginine(Nitro)
Atc = 2-Aminotetralin-2-carboxylic acid
Atcp = 4-Amino-3,5,6-trichlorpicolinic acid
Atmp = 4-Amino-2,2,6,6-tetramethylpiperidine
AtmpO = 4-Amino-2,2,6,6-tetramethylpiperidinyloxy
Atpc = 4-Amino-2,2,6,6-tetramethyl-4-piperidinecarboxylic acid
Atpm = 4-Amino-4-methoxycarbonyl-2,2,6,6-Tetramethylpiperidine
(4-Amino-2,2,6,6-tetramethyl-4-piperidinecarboxylic acid methyl ester)

TABLE 6-continued

ABBREVIATIONS USED FOR COMPOUNDS

Aud = 11-Aminoundecanoic acid
Ava = 5-Aminovaleric acid
Azt = Azetidine-2-carboxylic acid
BAla = β-Alanine
BApG = N,N-bis(3-aminopropyl)-glycine
BAPTA = 1,2-bis(2-Aminophenoxy)ethane-N,N,N',N'-tetraacetyl
Bip = Biphenylalanine
Boc = (tert-Butoxycarbonyl); [(1,1-dimethylethoxy)carbonyl]
BOP = Benzotriazoyloxytris(dimethylamino)phosphonium hexafluorophosphate
BPHD = N,N'-bis(2,2,6,6-tetramethyl-4-piperidinyl)-1,6-hexanediamine
BSH = 1,6-Bissuccinimidohexane
BtA = 3-Benzothienylalanine
BTAC = Benzene-1,3,5-tris-carboxyamido-6-caproyl
BTC = 1,3,5-Benzenetricarboxyl
Bz = Benzoyl
Bzl = Benzyl
CAcH = cis-2-Amino-1-cyclohexanecarboxylic acid
Cca; 2-Chlorocinnamic acid
CDF = p-Chloro-D-phenylalanine
ChA = α-Cyclohexylalanine
Chc = α-Cyano-4-hydroxycinnamoyl
ChG = α-Cyclohexylglycine
CHO = Chinese hamster ovary
CHTC = 1,3,5-Cyclohexanetricarboxyl
CHyp = cis-4-Hydroxy-proline
Cin = Cinnamoyl
CMeb = S-(4-Methylbenzyl) cysteine
CmF = (Z) p-Chloro-2,3-methanophenylalanine
Cmp = 4-Carboxymethylpiperazine
CpA = α-Cyclopropylalanine
CpG = α-Cyclopentylglycine
CpGΨ(CH$_2$N)Arg = CpG pseudo(CH$_2$NH) Arg
CPTA = trans-1,2-Diaminocyclohexane-N,N,N',N'-tetraacetyl
CTAC = Cyclohexane-1,3,5-tris-carbamido-ε-caproyl
Ctim = 13-Carboxytridecanimidyl
Cyh = Cyclohexylamine
Dabz = Diaminobenzoic acid
DArg(NO$_2$) = Nitro-Arginine
Dca = Dicyclohexylacetyl
Dcg = N,N'-Dicylcohexylguanidyl
DCM = Dichloromethane
DDA = 1,10-Decanediamine
DDD = Dodecanedioyl-
DDS = 2-Dodecen-1-ylsuccinyl
DEA = N,N'-Diethylethylenediamine
DhP = 3,4-Dehydroproline
Dhq = 2,3-Dehydroquinuclidine-3-carboxyl
DIC = Decahydroisoquinuclidine-3-carboxyl
DIEA = Diisopropylethylamine
Dmab = 4-Dimethylaminobenzylamine
Dmac = 4-Dimethylaminocinnamoyl
Dmb = 4-(Dimethylamino)benzyl
DmF = 2,4-Dimethylphenylalanine
DMF = Dimethyl formamide
DmK = ε-Dimethyllysine
Dmm = 2,6-Dimethylmorpholine
Dmp = 3-Dimethylaminopropylamine
DmtP = 5,5-Dimethyl-4-thiaproline

TABLE 6-continued

ABBREVIATIONS USED FOR COMPOUNDS

Dns = Dansyl (5-dimethylamino-1-naphthalenesulfonyl)
22Dp = 2,2-Diphenylpropionyl
33Dp = 3,3-Diphenylpropionyl
Dpa = Diphenylacetyl
Dpea = Diphenylethylamine
Dpma = Diphenylmethylamine
Dpr = 2,3-Diaminopropionic acid
DTP = Dithiobis-propionyl
DTPA = Diethylenetriaminepentaacetyl
Eac = $\epsilon$-Aminocaproic acid
Ecap = N-Ethoxycarbonyl-4-amino-piperidine (Ethyl 4-amino-1-piperidinecarboxylate)
EDA = 4,4'-Ethylenedianiline
EDP = 4,4'-Ethylenedipiperidine
EDTA = Ethylenediaminetetraacetyl
EDTP = Ethylenediaminetetrapropionic acid
EGS = Ethylene glcyol-bis-succinyl
EGTA = Ethylene glycol-bis($\beta$aminoethyl ether)-N,N,N',N'-tetraacetyl
EOPC = 1,1'-Ethylenebis(5-oxo-3-pyrrolidinecarboxyl)
ETTA = 2,2',2'',2'''-[Ethanediylidenetetrakis(thio)tetrakisacetyl
F2F = Difluorophenylalanine
F5bz = Pentafluorobenzoyl
F5c = 2,3,4,5,6-Pentafluorcinnamoyl
F5F = Pentafluorophenylalanine
F5pa = 2,3,4,5,6-Pentafluorocinnamoyl
F5po = 2,3,4,5,6-Pentafluorophenoxyacetyl
Fbz = para-Fluorobenzoyl
Flu = Fluorescein thiourea
Gaa = Guanidinoacetyl
GaP = 2-Guanidyl-3-(4-aminophenyl)propionic acid
Gbz = 4-Guanidinobenzoyl
Glt = Glutaryl
Gun = Guanidyl
HATU = O-(7-azabenzotriazol-1-yl)-1,1,3,3-tetramethyluronium hexafluorophosphate
HbQ = 4-Hydroxybutylglutamine
HDA = 1,6-Hexanediamine
HDD = Hexadecanedioyl
HF = Hydrogen fluoride
HFG = hexafluoroglutaroyl
HiG = Hexahydro-2-indanylglycine
HOAt = 1-Hydroxy-7-azabenzotriazole
hPhe = Homo-phenylalanine
HPLC = high performance liquid chromatography
Hxa = Hexanoic acid
Hyp = trans-4-Hydroxyproline
Ica = Indoline-2-carboxylic acid
Igl = $\alpha$-2-Indanylglycine
Ing = $\alpha$-1-Indanylglycine
Inp = Isonipecotic acid
Iq2a = 6,7-Dimethoxy-3,4-Dihydro-1-isoquinolineacetic Acid
Iq4a = 6,7-Dimethoxy-1,2,3,4-tetrahydro-1-isoquinolineacetic acid
Lau = Lauroyl
Leu(r)Leu = Leu-pseudo(CH$_2$NH)Leu
Leu$\Psi$(CH$_2$NH)Leu = Leu-pseudo(CH$_2$NH)Leu
LDMS = laser desorption mass spectrometry
mA$_2$Bz = 3,5-Diaminobenzoic acid
MaG = $\alpha$-Methallylglycine (2-amino-3-methyl-4-pentenoic acid)
Mapp = 4-(Methylamino)-1,2,2,6,6-pentamethylpiperidine
Matp = 4-(Methylamino)-2,2,6,6-tetramethylpiperidine
MatpO = 4-(N-methylamino)-2,2,6,6-tetramethylpiperidinyloxy
MBC = S-(4-methylbenzylcysteine
MBHA = Methylbenzhydrylamine
MC2Y = N-Methyl-O-2,6-dichlorobenzyl-tyrosine
Mca = 2-Methylcinnamic acid
Mcg = Monocyclohexylguanidyl
Meb = Methylbenzyl
MeP = 2,4-Methanoproline
Mes = Methanesulfonyl
MFE = (E)-2,3-Methanophenylalanine
MFF = meta-Fluorophenylalanine
Mosi = Methoxy-suberimido
Moti = 14-Methoxytetradecanediimidoyl
Mse = Methoxysebacyl
MTT = (3-(4,5)-Dimethyltriazol-2-yl)-2,5-diphenyl tetrazolium bromide
Nal = $\beta$-Naphthylalanine
Nap = Naphthoyl Nba = Norbornane-2-acetyl
Nbc = Norbornenedicarboxyl
Nbi = Norbornenedicarboximide
Nbn = 2-Aminonorbornane-2-carboxylic acid
Nc5G = N-Cyclopentylglycine
Nc6G = N-Cyclohexylglycine
Nc7G = N-Cycloheptylglycine
Nc8G = N-Cyclooctylglycine
Nig = N-2-Indanylglycine
NiK = $\epsilon$-Nicotinoyllysine
NMF = N-Methylphenylalanine
NSCLC = non-small cell carcinoma
OBS = O-Benzylserine
OBT = O-Benzylthreonine
OBY = O-Benzyltyrosine
OC2Y = O-2,6-Dichlorobenzyltyrosine
OCIY = O-2,6-Dichlorobenzyl-3,5-diiodotyrosoine
Oct = Octanoyl
Oic = Octahydroindole-2-carboxylic acid
OMe = O-Methyl
OMY = O-Methyltyrosine
OSY = Tyrosine O-sulfate ester
Paa = Phenylacetyl
Pac = 4-Aminocinnamic acid
PaF = p-Aminophenylalanine
Pal = $\beta$-Pyridylalanine
Pba = Phenylbutyryl
Pcc = trans-2-Phenyl-1-cyclopropanecarboxylic acid
PCF = p-Chlorphenylalanine
Pcpa = $\alpha$-Phenylcyclopentaneacetyl
PdF = p-Dicyclohexylguanidylphenylalanine
PFF = p-Fluorophenylalanine
PFS = Perfluorosuberoyl
PgF = p-Guanidinophenylalanine
PheOL = Phenylalaninol
PhG = Phenylglycine
Pip = Pipecolic acid ("homo-Pro")
PipA = $\beta$-3-Piperidylalanine
PNF = p-Nitrophenylalanine
Ppa = Phenylpropionyl
Pya = trans-3-(3-Pyridyl)acryloyl
PyAOP = 7-Azabenzotriazol-1-yloxytris(pyrrolidino)phosphonium hexafluorophosphate
PzK = $\epsilon$-Pyrazinoyllysine
PzO = 4-Pyrazinoylornithine
Saa = trans-Styrylacetic acid
SBEC = Sulfo-bis-ethoxycarbonyl
Sbl = Sebacoyl
SCLC = small cell lung carcinoma
Seb = Sebacyl
Sin = Sinapinyl (3,5-dimethoxy-4-hydroxycinnamoyl-)
Ste = Stearoyl
Sua = Sulfanilamide (4-Aminobenzenesulfonamide)
SUB = Suberyl
Suc = Succinyl
Sud = Sulfadiazine
SUIM = Suberimidyl
Sul = Sulindac
Tba = t-Butyl-acetyl
TDIM = Tetradecanediimidyl
TEA = Triethylamine
TFA = Trifluoroacetic acid
Tfmc = trans-4-(Trifluoromethyl)cinnamoyl
Tha = 3-(2-Thienyl)acryloyl
Thi = $\beta$-2-Thienylalanine
Thm = Thiomorpholine
Thz = Thiazolidine-4-carboxylic acid (4-thiaproline)
Tic = 1,2,3,4-Tetrahydroisoquinoline-3-carboxylic acid
TLC = thin layer chromatography
TLeu = tert-Leucine
TMF = 2,4,6-Trimethylphenylalanine
Tos = p-Toluenesulfonyl
Tpac = 2,2,5,5-Tetramethyl-3-(aminoethyl)-pyrroline-3-carboxamide
TREN = tris(2-Aminoethyl)amine
Trx = Tranexamic acid (trans-4-((Aminomethyl))cyclohexanecarboxylic acid)

What is claimed is:

1. The compound of structure:
2,3,4,5,6-Pentafluorocinnamoyl-D-Arginine-Arginine-Proline-Trans-4-hydroxyproline-Glycine-α-2-Indanylglycine-Serine-D-α-2-Indanylglycine-Octahydroindole-2-carboxylic acid-Arginine
or a pharmaceutically acceptable salt thereof.

2. The compound of the structure:
2,3,4,5,6Pentafluorocinnamoyl-Lysine-Lysine-Arginine-Proline-Trans-4-hydoxyproline-Glycine-α-Cylcopentylglycine-Serine-D-1,2,3,4-Tetrahydroisoquinoline-3-carboxylic acid-α-Cylcopentylglycine
or a pharmaceutically acceptable salt thereof.

3. The compound of structure:
2,3,4,5,6-Pentafluorocinnamoyl-D-ε-Nicotinoyllysine-4-(2-pyrazine carboxyl)ornithine Proline-Trans-4-hydroxyproline-Glycine-α-2-Indanylglycine-Serine-D-α-2-Indanylglycine-Octahydroindole-2-carboxylic acid-Arginine
or a pharmaceutically acceptable salt thereof.

4. The compound of structure:
2,3,4,5,6-Pentafluorocinnamoyl-p-Fluorophenylalanine-Arginine
or a pharmaceutically acceptable salt thereof.

5. The compound comprising the structure:
Dodecanedioyl-(D-Arginine-Pentaflurorphenylalanine-Arginine)$_2$
or a pharmaceutically acceptable salt thereof.

6. The compound of structure:
2,3,4,5,6-Pentafluorocinnamoyl-O-2,6-Dichlorobenzyltyrosine-4-Amino-2,2,6,6-tetramethylpiperidine
or a pharmaceutically acceptable salt thereof.

7. The compound of structure:
Dodecanedioyl-(D-Arginine-α-2-Indanylglycine-Arginine-4-(Methylamino)-2,2,6,6-tetramethylpiperidine)$_2$
or a pharmaceutically acceptable salt thereof.

8. The compound comprising the structure:
Ethylenediaminetetraacetyl-(O-2,6-Dichlorobenzyltyrosine-4-(Methylamino)-2,2,6,6-tetramethylpiperidine)$_4$
or a pharmaceutically acceptable salt thereof.

9. The compound of structure:
(5-dimethylamino-1-naphthalenesulfonyl-D-Arginine-α-2-Indanylglycine-Arginine)$_2$-1,10-Decanediame
or a pharmaceutically acceptable salt thereof.

10. The compound of structure:
Dodecanedioyl-(D-Arginine-β-2Naphthylalanine-Arginine-4-(methylamino)-2,2,6,6-tetramethylpiperidine)$_2$
or a pharmaceutically acceptable salt thereof.

11. The compound of structure:
Decanedioyl-(-4-Aminocinnamic acid-α-2-Indanylglycine-4-amino-2,2,6,6-tetramethylpiperidine),(-Lysine-D-Arginine-Arginine-Proline-Trans-4-hydroxyproline-Glycine-α-2-Indanylglycine-Serine-D-α-2-Indanylglycine-Octahydroindole-2-carboxylic acid-Arginine),
or a pharmaceutically acceptable salt thereof.

\* \* \* \* \*